United States Patent
Ohtake et al.

(10) Patent No.: US 8,513,608 B2
(45) Date of Patent: Aug. 20, 2013

(54) COATING FILM INSPECTION APPARATUS AND INSPECTION METHOD

(75) Inventors: Hideyuki Ohtake, Kariya (JP); Yuzuru Uehara, Chiryu (JP); Jun Takayanagi, Anjo (JP)

(73) Assignee: Aisin Seiki Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 13/581,123

(22) PCT Filed: Feb. 21, 2011

(86) PCT No.: PCT/JP2011/000950
§ 371 (c)(1),
(2), (4) Date: Aug. 24, 2012

(87) PCT Pub. No.: WO2011/105040
PCT Pub. Date: Sep. 1, 2011

(65) Prior Publication Data
US 2012/0326037 A1    Dec. 27, 2012

(30) Foreign Application Priority Data

Feb. 26, 2010  (JP) ................................. 2010-042492
Dec. 17, 2010  (JP) ................................. 2010-281408

(51) Int. Cl.
*G01J 5/02*   (2006.01)
(52) U.S. Cl.
USPC .................................. 250/341.8; 250/341.1
(58) Field of Classification Search
USPC ................................. 250/341.1, 341.3, 341.8
See application file for complete search history.

(56) References Cited

U.S. PATENT DOCUMENTS

| 7,551,269 B2 | 6/2009 | Itsuji | |
| 2005/0098728 A1* | 5/2005 | Alfano et al. | 250/341.8 |
| 2008/0315098 A1 | 12/2008 | Itsuji | |
| 2010/0090112 A1* | 4/2010 | Kawada et al. | 250/338.4 |
| 2010/0195092 A1* | 8/2010 | Ohtake | 356/51 |
| 2010/0235114 A1* | 9/2010 | Levy et al. | 702/40 |

FOREIGN PATENT DOCUMENTS

| JP | 5-288690 A | 11/1993 |
| JP | 9-259435 A | 10/1997 |
| JP | 3214190 B2 | 7/2001 |
| JP | 2004-101257 A | 4/2004 |
| JP | 2004-340763 A | 12/2004 |
| JP | 2006-153845 A | 6/2006 |
| JP | 4046158 B2 | 2/2008 |
| JP | 4084817 B2 | 4/2008 |
| JP | 2008-246347 A | 10/2008 |
| JP | 2009-069138 A | 4/2009 |
| JP | 2009-075069 A | 4/2009 |
| JP | 2009-200461 A | 9/2009 |

OTHER PUBLICATIONS

International Search Report, PCT/JP2011/000950, May 31, 2011.
English translation of International Preliminary Report on Patentability for PCT/JP2011/000950 dated Sep. 18, 2012.

* cited by examiner

*Primary Examiner* — Mark R Gaworecki
(74) *Attorney, Agent, or Firm* — Sughrue Mion, PLLC

(57) ABSTRACT

The coating film inspection apparatus according to one embodiment of the present invention comprises a terahertz-wave generator that generates a terahertz-wave; an irradiation optical system that irradiates, with the terahertz-wave, a sample with a film formed thereon; a terahertz-wave detector that detects a terahertz-wave reflected at the sample; and a control unit that shows an electric field intensity of the detected terahertz-wave in wave form data on a time axis to detect a plurality of peaks from the wave form data, and also calculates film thickness on the basis of time difference between peaks.

4 Claims, 26 Drawing Sheets

PULSE WAVE FORM OF 17 fs

PULSE WAVE FORM OF 37 fs

FIG. 12

| SUBSTRATE \ KIND | COLORED FIRST LAYER | METALLIC SECOND LAYER | CLEAR THIRD LAYER |
|---|---|---|---|
| METAL SUBSTRATE | (1) | (2) | (3) |
| RESIN SUBSTRATE | (4) | (5) | (6) |

| DETAIL OF LAYERS | REFRACTIVE INDEX | DELAY TIME (fs) | FILM THICKNESS (μm) |
|---|---|---|---|
| FIRST LAYER (CLEAR) 20μm | 1.8 | 220 | 18 |
| SECOND LAYER (MICA) 10μm | 1.4 | 100 | 10 |
| THIRD LAYER (COLORED) 30μm | 2.1 | 440 | 31 |

| PAINT AND SUBSTRATE | COLORED | METALLIC | CLEAR | MICA | ABS RESIN SUBSTRATE |
|---|---|---|---|---|---|
| MEASURED REFRACTIVE INDEX | 2.1 | 2.2 | 1.8 | 1.4 | 1.5 |

Z ⊙ TERAHERTZ-WAVE TRAVELING DIRECTION

⟷ POLARIZATION DIRECTION

⟵---⟶ CRYSTAL AXIS DIRECTION

Z ⊙ TERAHERTZ-WAVE TRAVELING DIRECTION

⟷ POLARIZATION DIRECTION

⟵---⟶ CRYSTAL AXIS DIRECTION

Z ⊙ TERAHERTZ-WAVE TRAVELING DIRECTION

◄──► POLARIZATION DIRECTION

◄---► CRYSTAL AXIS DIRECTION

Z ⊙ TERAHERTZ-WAVE TRAVELING DIRECTION

◄──► POLARIZATION DIRECTION

◄---► CRYSTAL AXIS DIRECTION

COATING FILM INSPECTION APPARATUS AND INSPECTION METHOD

CROSS REFERENCE TO RELATED APPLICATIONS

This application is a National Stage of International Application No. PCT/JP2011/000950 filed Feb. 21, 2011, claiming priority based on Japanese Patent Application Nos. 2010-042492 filed Feb. 26, 2010 and 2010-281408 filed Dec. 17, 2010, the contents of all of which are incorporated herein by reference in their entirety.

TECHNICAL FIELD

The present invention relates to a coating film inspection apparatus and method, for measuring coating qualities such as film thickness and unevenness of coating.

BACKGROUND ART

In industrial products such as automobiles, various coatings are applied onto a base material (foundation), and an inspection apparatus for nondestructively inspecting a coating film is used. The coating film inspection apparatus is able to inspect nondestructively film thickness, gloss etc. of coating by use of a laser, ultrasonic wave, X-ray etc.

As an inspection apparatus of film thickness, for example, PL 1 (Japanese Patent No. 3214190) is known. The inspection apparatus is able to measure film thickness by using an optical sensor and an eddy-current sensor to calculate the difference between the distance up to a coating film surface measured by the optical sensor and the distance up to a conductor measured by the eddy-current sensor.

The inspection apparatus described in PL 2 (Japanese Patent No. 4084817) measures film thickness using a reflection intensity of P-polarized light. The inspection apparatus intends to inspect a thin film of not more than 200 nm, by not depending on randomly-polarized light but using P-polarized light.

PL 3 (Japanese Patent No. 4046158) relates to an inspection apparatus using terahertz-waves. Terahertz-waves have an intermediate quality of light waves and electric waves, and pass through coating films containing a polymeric material. The inspection apparatus irradiates a sample with terahertz-pulses due to femtosecond laser excitation, and calculates the film thickness by measuring the difference in time between respective peaks appearing in reflected waves.

Further, also for external appearances of metallic coatings, following approaches are tried in order to obtain an objective inspection indicator.

Coatings applied to articles such as automobiles are an important element for determining the external appearance of the article in addition to the purpose of anticorrosion, and, therefore, it is necessary to measure objectively the coating external appearance. In particular, since automobiles are mass-produced and require high-quality coatings, it is required to perform the coating inspection precisely in a short time. Coatings of automobiles are classified roughly into a solid coating and a metallic coating. Since the solid coating includes a binder containing pigment, optical properties of hue and brightness are measured easily by a measurement apparatus. On the other hand, the metallic coating includes a clear layer and a base layer, and the base layer contains, in addition to pigment, a scaly brightness material (an aluminum flake, mica flake or the like). Consequently, corresponding to the orientation state of flakes, reflected light having a directional property is generated to generate a shiny feeling peculiar to metallic coatings. In the case where the orientation state or distribution state of flakes are not even, it is recognized as color unevenness, and, therefore, the inspection of color unevenness of metallic coatings is required. However, the color unevenness of metallic coatings can not be expressed by hue, brightness etc., differing from solid coatings, and, in the existing circumstances, there is no option but to depend on visual inspection.

Under such circumstances, several attempts have been performed for evaluating objectively metallic coatings.

PL 4 (Japanese Patent Application Laid-Open No. 2009-69138) relates to a method for evaluating color unevenness by making light enter every measuring point on a metallic coating with not less than two light axes and by measuring color or reflection intensity of each reflected light.

PL 5 (Japanese Patent Application Laid-Open No. 2008-246347) relates to an inspection apparatus for discriminating the surface state of flakes by extracting an characteristic quantity of metallically coated surface with a microscope and comparing the observed characteristic quantity with characteristic quantities registered in a database. As the characteristic quantity, a flake size, density, evaluated value showing the degree of rising and falling, or an evaluated value showing the surface state of flakes contained in the metallic coating is used.

PL 6 (Japanese Patent Application Laid-Open No. 05-288690) relates to an inspection apparatus for discriminating color unevenness etc. by processing statistically measured values. The inspection apparatus scans the metallic coating surface to measure continuously brightness, performs Fourier-transform of the change in measured brightness to perform analysis in frequency region, and discriminates the magnitude of amplitude at a specified frequency (length) as color unevenness.

CITATION LIST

Patent Literature

PL 1: Japanese Patent No. 3214190
PL 2: Japanese Patent No. 4084817
PL 3: Japanese Patent No. 4046158
PL 4: Japanese Patent Application Laid-Open No. 2009-69138
PL 5: Japanese Patent Application Laid-Open No. 2008-246347
PL 6: Japanese Patent Application Laid-Open No. 05-288690

SUMMARY OF INVENTION

Technical Problem

However, inspection apparatuses described in above Patent Documents do not deal with film thickness measurement for measuring film thickness of each layer of a multilayer film, and can not measure each layer of a multilayer film. For example, the measurement apparatus described in PL 1 measures the distance up to the coated film surface by an optical measurement and measures the distance up to the conductor by eddy current measurement, and, therefore, it can not measure each layer of a multilayer film.

Inspection apparatuses described in PL 4 to 6 relate to an inspection apparatus for metallic coatings. These inspection apparatuses perform measurement with a plurality of light axes or measurement at a plurality of measuring points on a metallic coating, and inspect color unevenness by statistical processing of a plurality of measured values. That is, they integrate (average) a plurality of measured values by a statistical processing. Consequently, difference of altitude caused by a curved surface and minute color unevenness are also averaged to make the performance of precise inspection difficult.

For example, in the apparatus described in PL 4, the measurement must be performed using a plurality of light axes at each of a plurality of measuring points, which requires much time for the measurement. That is, since it is impossible to irradiate the same point with a plurality of light axes, the measuring time increases as the number of light axes increases. Further, in the Document, sufficient analysis is not performed about the relation between the measuring result and flakes that generate color unevenness, and, therefore, it is difficult to say that precise measuring results are obtained.

In the inspection apparatus described in PL 5, micro images must be taken with a microscope, but the use of a microscope in production lines in factories is not easy. In addition, micro images on the coating surface change moment by moment directly after the coating, and, therefore, the application of the method to so-called wet coatings is difficult.

In the inspection apparatus described in PL 6, difference of altitude and minute color unevenness are averaged by the statistical processing of a plurality of measured values, and precise inspection is not necessarily expected.

As described above, in conventional inspection apparatuses shown in PL 4 to 6, the color unevenness is inspected by performing measurements by means of a plurality of light axes or at a plurality of measuring points on a metallic coating and by the statistical processing of a plurality of measured values. Consequently, much time is required for the measurement, and it is difficult to apply a conventional inspection method to a manufacturing process for which mass production is required. In conventional inspection methods, a metallic coated surface is scanned to obtain a plurality of measured values, and these measured values are subjected to statistical processing to be added (averaged). Consequently, minute color unevenness is also averaged, which makes it difficult to perform precise inspection.

Further, since the conventional inspection method measures the amount of reflected light at different measuring points on a metallic coating and grasps relative difference in measured values as color unevenness, it can not grasp the evenness of flake orientation. Incidentally, although in PL 5, a microscope is used to image flakes, the imaging is performed only for the surface of a metallic coating, and it is impossible to detect the flake orientation.

In order to solve the above problems, the inspection apparatus of coating according to the present invention includes a terahertz-wave generator which generates terahertz waves, an irradiation optical system which irradiates, with the terahertz-wave, a sample with a film formed thereon, a terahertz-wave detector which detects the terahertz waves reflected by the sample, and a control unit which, along with representing the electric field intensity of the detected terahertz waves in wave form data on a time-axis and detecting a plurality of peaks from the wave form data, calculates film thickness on the basis of time difference between the peaks.

The control unit detects a plurality of peaks from the wave form data according to a peak pattern which has been previously input.

The control unit detects peaks in the descending order of amplitude from the wave form data.

The control unit detects a plurality of peaks that exists in the time range corresponding to a film thickness range that has previously been input.

The control unit detects a plurality of peaks that exists in a range of intensity ratio that has previously been input.

Further, another embodiment of the coating film inspection apparatus according to the present invention includes a terahertz-wave generator that generates terahertz-waves, an irradiation optical system that irradiates a metallic coated sample with the terahertz-waves, a terahertz-wave detector that detects a plurality of polarized components of terahertz-waves reflected by the sample, and a control unit that calculates an index value of the metallic coated sample on the basis of the detected plurality of polarized components.

The coating film inspection apparatus additionally includes rotation means for rotating the terahertz-wave detector by a prescribed angle relative to the light axis of reflected terahertz-waves to make it possible to detect a plurality of polarized components.

The prescribed angle is approximately 45°, and the terahertz-wave detector detects two polarized components before and after the rotation.

The terahertz-wave detector includes a dipole antenna type detector. The terahertz-wave detector includes an EO crystal.

According to the present invention, a plurality of peaks is detected from wave form data, and the film thickness can be calculated on the basis of the difference in times between peaks.

Further, false detection of multiple reflection, noise or the like as a peak can be avoided by detecting a plurality of peaks from wave form data according to a peak pattern that has previously been input.

In addition, false detection of multiple reflection, noise or the like as a peak can be avoided by detecting peaks in the descending order of amplitude in wave form data. Furthermore, a measurement error caused by false detection of a peak can also be prevented by previously inputting the film thickness range and intensity ratio range of a sample to be measured.

According to another embodiment of coating film inspection apparatus according to the present invention, it is possible to grasp the orientation state of flakes of a metallic coating by irradiating a coated sample with terahertz-waves and detecting a plurality of polarization components in terahertz-waves reflected from the coated sample. Reflected terahertz-waves include complex permittivity and polarization as information intrinsic for the reflection surface of a metallic coating. The complex permittivity includes such information as a refractive index, an absorption index and an electric conductivity, and the polarization includes information of a material that disturbs polarization in a reflection surface or penetration region. When no color unevenness exists in a metallic coating, flakes inside the metallic coating are arranged randomly to disturb the polarization of reflected terahertz-waves. On the other hand, when color unevenness exists in a metallic coating, flakes are oriented in a specified direction, and the surface of the metallic coating has polarization properties as a diffraction grating in the frequency region of terahertz-waves. Accordingly, by measuring a plurality of polarization components in reflected terahertz-waves and comparing these polarization components, it is possible to decide whether the metallic coating is good or bad. That is, according to the present invention, the polarization component of reflected terahertz-waves including information of orientation state of flakes can directly be detected, and, therefore, no statistic arithmetic processing on the basis of a plurality of measurement results are required, differing from conventional techniques, to enable the inspection to be performed in a short time. Further, there is no averaging of detected information with statistical processing, to make precise inspection possible.

Terahertz-waves have such a property as to pass through resin, and, therefore, even a resin through which visible light does not pass may be inspected.

Furthermore, by rotating the detection means by a prescribed angle relative to the light axis of reflected terahertz-waves, a plurality of polarization components in the reflected terahertz-waves can be detected. When a dipole antenna is used as detection means, a situation where a detected value of the polarization component is zero can be avoided by setting the rotation angle of the detection means to be 45°.

When an EO crystal is used as detection means, no alignment adjustment after the rotation of the EO crystal is required, and effective measurement is possible.

BRIEF DESCRIPTION OF DRAWINGS

FIG. 12 is a drawing of a peak pattern according to the first embodiment of the present invention.

DESCRIPTION OF EMBODIMENTS

Hereinafter, embodiments of the present invention will be explained with reference to the drawings.

First Embodiment (Overall Configuration)

Figure 1:
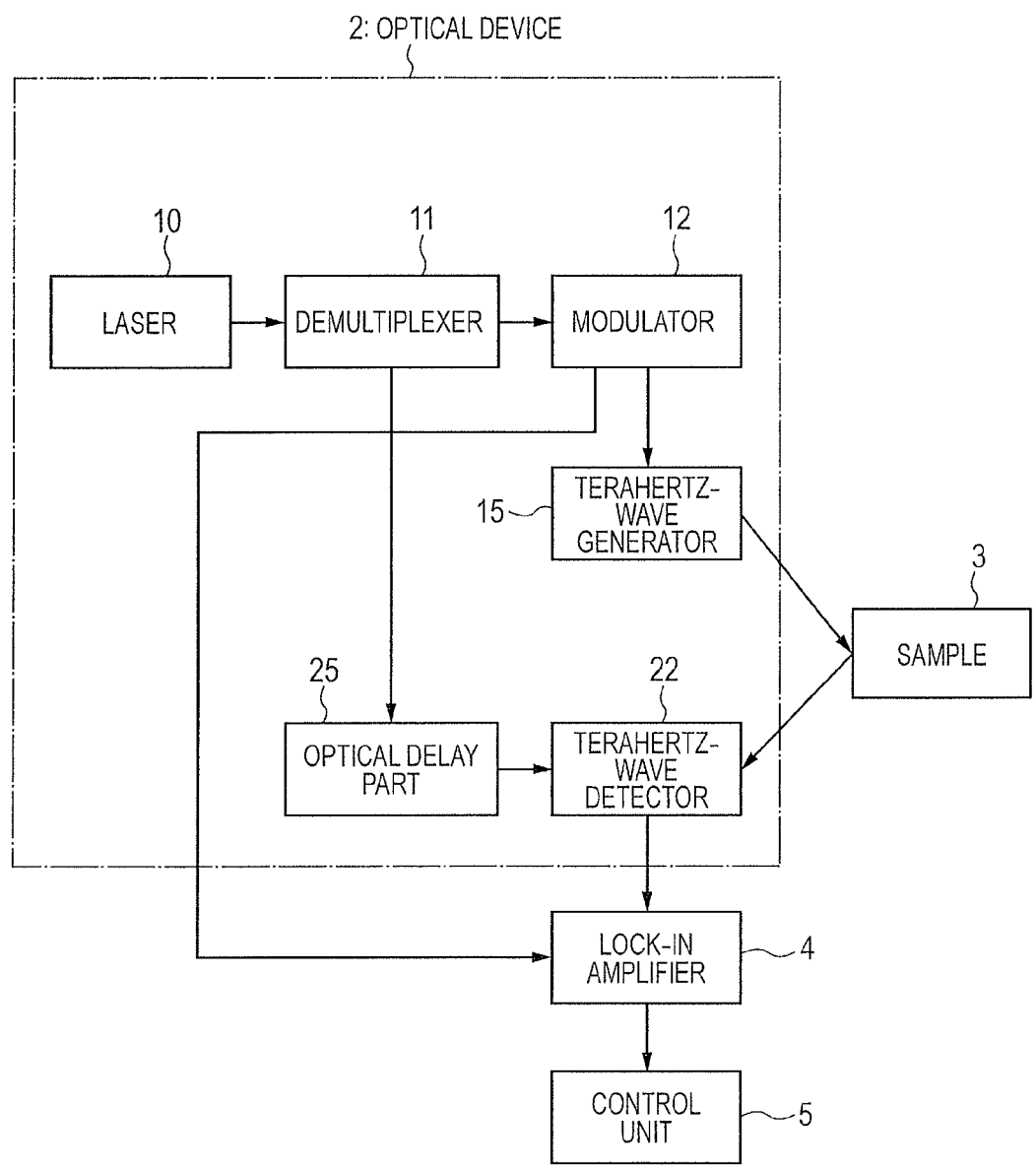
FIG. 1 is a schematic view of an inspection apparatus according to a first embodiment of the present invention.

FIG. 1 is a schematic configuration diagram of the coating film inspection apparatus according to the first embodiment of the present invention.

An inspection apparatus 1 includes an optical device 2 that irradiates a sample 3 with terahertz-waves and detects reflected waves, a lock-in amplifier 4 that amplifies synchronously the detection signal of reflected waves, and a control unit 5 for controlling the inspection apparatus. The optical device 2 includes a laser 10, a demultiplexer 11, a modulator 12, a terahertz-wave generator 15, a terahertz-wave detector 22 and an optical delay part 25.

Laser light excited by the laser 10 is demultiplexed into the fundamental wave and the second harmonic wave by the demultiplexer 11. The fundamental wave is modulated into pulses of a prescribed frequency by the modulator 12 and is made to enter the terahertz-wave generator 15. Terahertz-waves radiated from the terahertz-wave generator 15 are irradiated to the sample 3, and reflected waves enter the terahertz-wave detector 22. On the other hand, the second harmonic wave demultiplexed by the demultiplexer 11 is used as probe light. The probe light is delayed by the optical delay part 25, and is made to enter the terahertz-wave detector 22. The terahertz-wave detector 22 detects reflected waves from the sample 3 at the timing of the probe light. The lock-in amplifier 4 detects and integrates detected current in synchronization with modulation frequency to perform signal amplification with a high SN ratio. The signal amplified by the lock-in amplifier 4 is input to the control unit 5 as measured data. The control unit 5 is able to analyze measured data from the lock-in amplifier 4 and to decide coating qualities such as film thickness.

(Optical Device)

Figure 2:
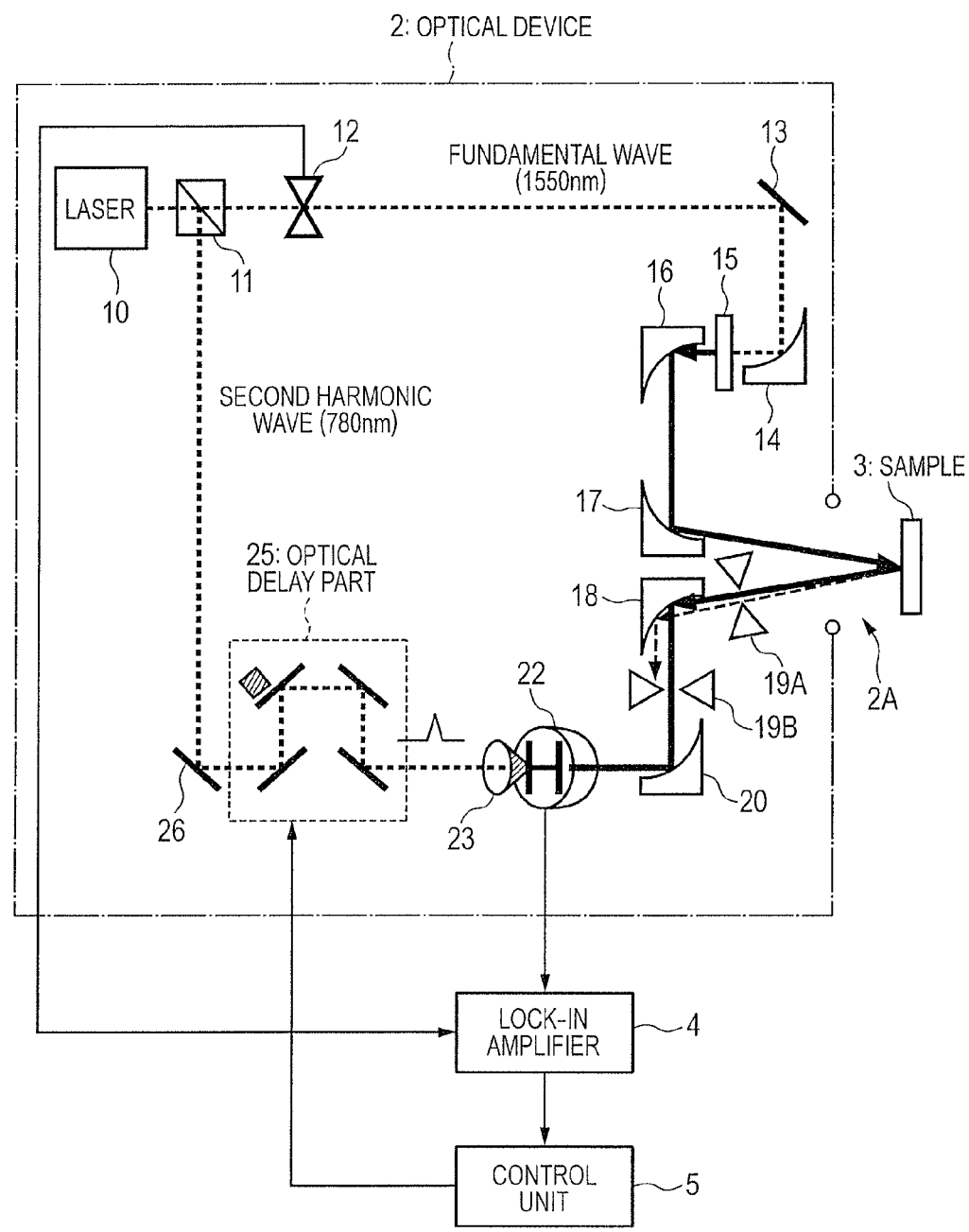
FIG. 2 is a block diagram of the inspection apparatus according to the first embodiment of the present invention.

FIG. 2 is a block diagram showing the detail of the optical device 2.

The optical device 2 includes a femtosecond fiber laser 10, a dichroic mirror 11, a chopper (modulator) 12, a mirror 13, a paraboloidal mirror 14 for condensing the fundamental wave, a DAST (terahertz-wave generator) 15, off-axis paraboloidal mirrors 16, 17, 18 and 20, a diaphragm 19, a terahertz-wave detector 22, a condenser lens 23, an optical delay part 25, and a mirror 26. The optical device 2 is sealed from the outside by a housing, wherein it is desirable to dehumidify, to fill nitrogen gas into, or to evacuate the inside of the housing. The configuration can prevent terahertz-waves from being absorbed by moisture in air.

The femtosecond fiber laser 10 generates light of 1550 nm by exciting an optical fiber doped, for example, with Er (erbium) by exciting light. The light is made to resonate between a pair of mirrors, and is output as a high-power light pulse via a polarizing beam splitter. The output light pulse includes the fundamental wave of 1550 nm component and the second harmonic wave of 780 nm component. In ordinary fiber lasers, a 1 μm zone or a 1.5 μm zone is the fundamental wave. When a dipole antenna of a GaAs substrate is used as the terahertz-wave detector 22, it is desirable to generate the second harmonic wave as probe light.

The dichroic mirror 11 is configured by multiple layer-coating alternately dielectric materials having different refractive indices on a white board glass, and separates the light pulse output from the femtosecond fiber laser 10 into the fundamental wave of the 1550 nm component and the second harmonic wave of 780 nm component. In the embodiment, the fundamental wave of 1550 nm component has an intensity of about 100 mW and a pulse width of 17 fs, and the second harmonic wave of 780 nm component has an intensity of about 10 mW and a pulse width of 37 fs. The fundamental wave of 1550 nm is used for generating terahertz-waves, and the second harmonic wave of 780 nm is used as probe light in the terahertz-wave detector. Incidentally, the present invention is not limited to these numerical values but may use other numerical values.

It is also possible to use a beam splitter for the fundamental wave in place of the dichroic mirror, and to arrange a wavelength conversion element between the beam splitter and the mirror 26. The beam splitter has desirably a wavelength band as wide as possible. And, in order not to extend the pulse width, the thickness of the element of the beam splitter is desirably not more than 0.5 mm.

Furthermore, when a laser that oscillates at a single central wavelength, such as a titanium sapphire laser, is used as a laser light source, the fundamental wave may be split by a beam splitter.

The chopper 12 is provided on the optical path of the fundamental wave passed through the dichroic mirror 11, and may be replaced by an acousto-optical element (AOM) or an electro-optical element (EOM). The modulation frequency by the chopper 12 is desirably a comparatively high value, such as approximately 1/10 of the repetition frequency of the laser. In the embodiment, the modulation frequency of 1 kHz is used. The chopper 12 may output a signal of the modulation frequency, and the modulation frequency is connected to the lock-in amplifier 4 and the control unit 5. According to the configuration, the lock-in amplifier 4 may perform the detection synchronized with the modulation frequency.

The mirror 13 directs the optical path of the fundamental wave having been modulated by the chopper 12 to the paraboloidal mirror 14 for condensing the fundamental wave. The paraboloidal mirror 14 for condensing the fundamental wave is arranged so as to condense the fundamental wave reflected by the mirror 13 to DAST.

The DAST (4-dimethylamino-N-methyl-4-stilbazolium tosylate) 15 is an organic non-linear optical crystal, and is known as an organic non-linear optical crystal having a high optical constant. The use of a femtosecond laser of ultrashort pulses makes it possible to generate terahertz-waves of not less than several tens THz.

In order to generate terahertz-waves, the use of an antenna is also possible, instead of a non-linear crystal. However, since transmissive antenna are easily influenced by the absorption and dispersion by the substrate and silicon lens, occasionally the generation of short pulses becomes difficult. The use of a reflective antenna makes it possible to avoid the influence of a silicon lens. However, even when a reflective antenna is used, there is such probability that electromagnetic waves are radiated in the case of a substrate having a large permittivity to make the output power of terahertz-waves small. On the other hand, a non-linear crystal can generate terahertz-waves only by condensing laser light and can eliminate the above problem.

Incidentally, in the embodiment, DAST is not an only usable material, but a non-linear crystal for laser wavelength conversion such as $LiNbO_3$, $MgO/LiTaO_3$, BBO, LBO or KTP, or a semiconductor crystal such as ZnTe, GnSe, GaP or GaAs may be used. KDP, ADP, $KNbO_3$, $BaTiO_3$, or a lead-based or zirconium-based ferroelectric crystal may also be used. Furthermore, a lead-based relaxor such as PMN, PZN and PZT, or a quantum paraelectric material-based relaxor material such as $KTa_{1-x}Nb_xO_3$, $K_{1-x}Li_xTaO_3$ and $Sr_{1-x}Ca_xTiO_3$ may also be used.

Terahertz-waves generated by the DAST 15 are reflected by off-axis paraboloidal mirrors 16 and 17, and are irradiated to the sample 3. Terahertz-waves reflected from the sample 3 are condensed by off-axis paraboloidal mirrors 18 and 20 and enter the terahertz-wave detector 22. Incidentally, the housing that covers the optical device 2 is provided with a window 2A, wherein terahertz-waves pass through the window 2A and are irradiated to the sample 3, and terahertz-waves having been reflected by the sample 3 also pass through the window 2A and enter the optical device 2. Incidentally, the window 2A is desirably closed with a transparent member, in order not to deteriorate the sealing property of the housing of the optical device 2.

Off-axis paraboloidal mirrors 18 and 20 make terahertz-waves having been reflected by the coated sample 3 condense to the terahertz-wave detector 22. As described later, between the sample 3 and the paraboloidal mirror 18, a diaphragm 19A is provided, and, between paraboloidal mirrors 18 and 20, a diaphragm 19B is provided. Diaphragms 19A and 19B are adjusted so that only the terahertz-wave having specularly been reflected by the sample 3 enters the terahertz-wave detector 22.

The terahertz-wave detector 22 is formed on a substrate of a photoconductive semiconductor thin film (such as low-temperature-grown GaAs) with metal electrodes having a gap as a dipole antenna. On one side of the substrate, a hemisphere lens is provided, and terahertz-waves having entered the hemisphere lens are converged to the gap part of the dipole antenna. On the other side of the substrate, a condenser lens 23 is arranged, and the condenser lens 23 converges femtosecond probe light. The probe light having been converged is irradiated to the gap of the dipole antenna to generate a carrier on the substrate. The carrier is accelerated by an oscillatory electric field going with the terahertz-wave, and there flows a momentary current that is proportional to the electric field of the terahertz-wave. By measuring the current, the intensity of electric field of terahertz-pulse waves can be measured.

The optical delay part 25 includes a fixed mirror and a movable mirror, and, corresponding to the position of the movable mirror, the delay of the probe light is determined. That is, by changing the optical path length of the probe light, the timing when the probe light arrives at the terahertz-wave detector 22 can arbitrarily be determined. Accordingly, by measuring electric fields of terahertz-waves that arrive repeatedly, while changing the timing, it becomes possible to sample the wave form of terahertz-waves.

The lock-in amplifier 4 performs signal amplification with a high SN ratio by detecting and integrating a current to be detected in synchronization with the modulation frequency. That is, to the lock-in amplifier 4, the signal of the modulation frequency in the chopper 2 is input, and, in synchronization with the signal, the lock-in amplifier 4 can amplify the weak current to be detected from the terahertz-wave detector 22. The signal amplified by the lock-in amplifier 4 is input to the control unit 5 as measured data.

The control unit 5 is configured, for example, by a personal computer, and synchronizes the chopper 12, the optical delay part 23 and the lock-in amplifier 4 at the modulation frequency. The control unit 5 may also analyze the measured data from the lock-in amplifier 4 and decide the coating quality such as film thickness of the sample 3.

(Laser, Demultiplexer)

Figure 3:
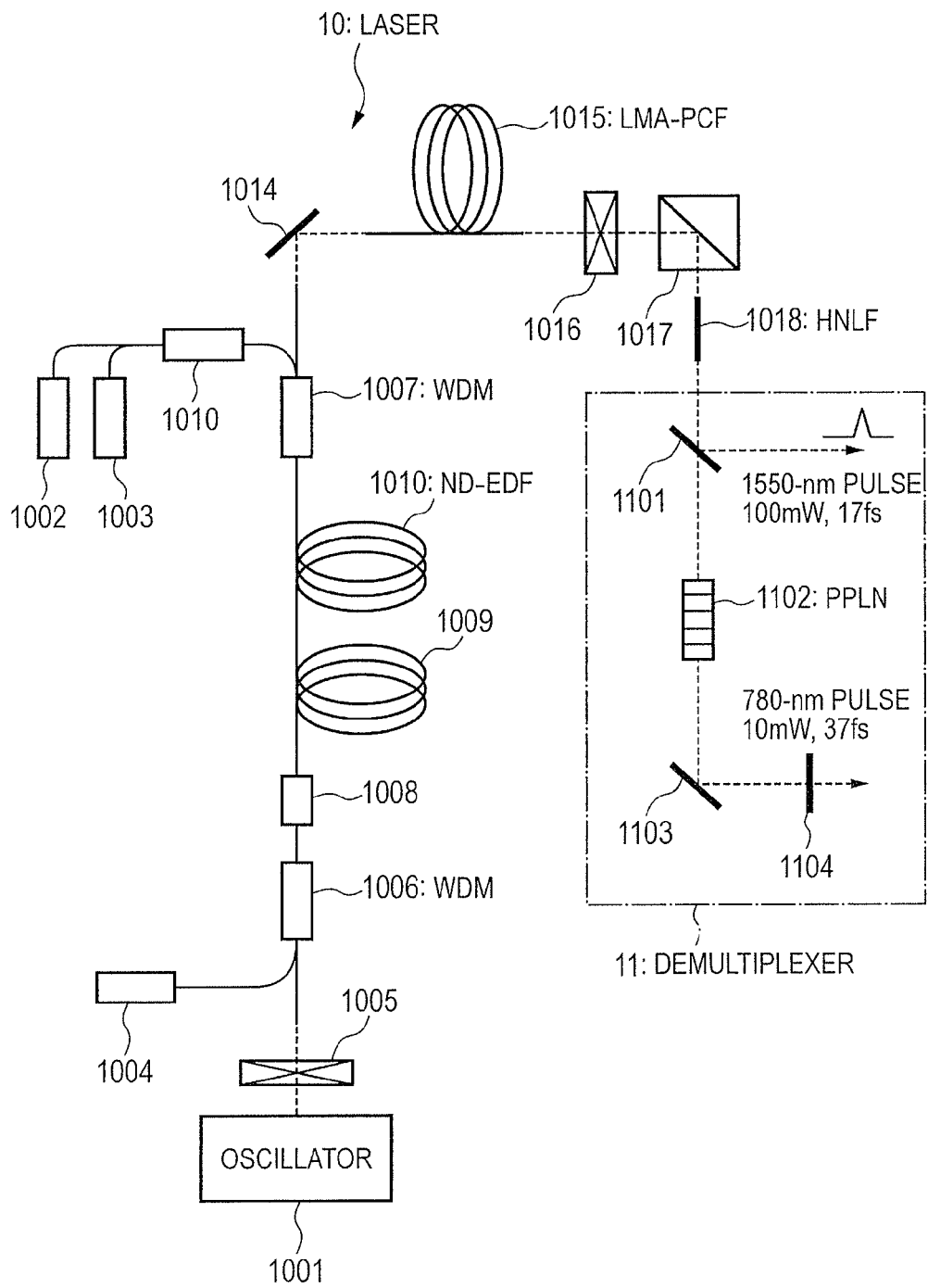
FIG. 3 is a block diagram of a laser and a demultiplexer according to the first embodiment of the present invention.

With reference to FIG. 3, the detailed configuration of the laser 10 and the demultiplexer 11 will be explained.

The laser 10 is an optical fiber laser, and includes an oscillator 1001 for excitation, laser diodes 1002 to 1004 that are pumping light sources, a $\lambda/2$ plate 1005, WDM (wavelength-division multiplexing) couplers 1006 and 1007, a polarized wave combiner 1008, a single mode fiber 1009, an erbium-doped fiber 1010, a polarization beam combiner 1010, a reflector 1014, an LMA-PCF (Large Mode Area-Photonic Crystal Fiber) 1015, a $\lambda/2$ plate 1016, a polarization beam splitter 1017, and an HNLF (Highly Non-Linear Fiber) 1018.

The oscillator 1001 is an Er-added fiber laser, and may generate a short pulse signal light. The pulse width is desirably approximately 300 fs. Incidentally, an Yb-added fiber laser, instead of Er, may also be used, or a solid laser such as titanium-sapphire laser may also be used.

When selecting a laser, the film thickness must be taken into consideration. For example, when performing the measurement of a film thickness having thickness of 10 µm and a refractive index of 2, the difference in optical paths between the reflected wave on the front side and the reflected wave on the back side of the film is 10 µm×2×2=40 µm. The difference in time on this occasion is $40 \times 10^{-6}/3 \times 10^8 = 1.3 \times 10^{-13} = 130$ fs. Accordingly, the pulse width of terahertz-waves, too, is desirably approximately 130 fs. When laser pulse is of about 100 fs, the pulse width of terahertz-waves generated by the antenna and the silicon lens is about 1 ps. Even if a non-linear crystal is used, the pulse width of terahertz-waves is about 500 fs. The reason why the pulse width is broadened as describe above is due to absorption and dispersion when the pulse passes through the antenna and silicon lens, phase mismatching and absorption of the non-linear crystal, etc. Incidentally, although the phase mismatching, absorption etc. may be reduced by making the non-linear crystal thin, at the same time, the output of terahertz-waves reduces. Accordingly, it is desirable to make a laser pulse be of a short pulse, without thinning the non-linear crystal.

The repetition frequency of the excited signal light is 50 MHz. By setting the repetition frequency to be high, it is possible to enlarge the SN ratio of the signal that is detected by the terahertz-wave detector 22. On the other hand, when the repetition frequency is set to be too high, the pulse interval is narrowed to narrow a scannable range in the time region of the detection signal. Consequently, it is necessary to use a repetition frequency corresponding to the film thickness to be measured.

The $\lambda/2$ wavelength plate 1005 is provided between the oscillator 1001 and the WDM coupler 1006. When outputting the signal light of the oscillator 1001 to a polarization-maintaining fiber, the oscillator 1001 can directly be connected with the WDM coupler 1006 without using the $\lambda/2$ wavelength plate 1005.

Laser diodes 1002, 1003 and 1004 are pump light sources for exciting the fiber. In the embodiment, pump light sources are provided on both sides of the fiber, but a pump light source may be provided only on one side. Laser diodes 1002, 1003 and 1004 may output pump light of 1480 nm and 400 mW, but they may be one that outputs pump light of 980 nm etc.

The pump light of laser diodes 1002 and 1003 is injected into the erbium-doped fiber 1010 via a polarization beam combiner and the WDM 1007. The pump light of the laser diode 1004 is injected into the single mode fiber 1001 and the erbium-doped fiber 1010 with signal light from the oscillator 1001 via the WDM coupler 1006.

It does not matter whether the erbium-doped fiber 1010 is a polarization-maintaining fiber or not. When the erbium-doped fiber 1010 is a polarization-maintaining fiber, it is possible to design high output by injecting exciting light along a slow axis and a fast axis of the polarization fiber by the polarized wave combiner 1008.

The exciting light in the erbium-doped fiber 1010 is amplified while broadening the pulse width thereof by a normal dispersion effect. Consequently, it becomes possible to avoid a non-linear effect. Incidentally, the pulse width of laser output from the WDM coupler 1010 had a pulse width 1 ps, and an output 400 mW.

The laser pulse from the WDM coupler 1007 is input to the LMA-PCF 1015 via the reflector 1014. The LMA-PCF 1015 has such a nature as abnormal dispersion, and makes the passing laser disperse abnormally to narrow the pulse width of laser. The pulse width of the laser output from the LMA-PCF 1015 is narrowed down to 50 fs. The laser is input to an HNLF (Highly Nonlinear Fiber) 1018 via the $\lambda/2$ plate 1016 and the polarization beam splitter 1017.

The HNLF 1017 has large non-linearity, and can narrow a pulse width 50 fs to 17 fs by non-linear pulse compression. Incidentally, without providing the λ/2 plate 1012 and the polarization beam splitter 1017, the LMA-PCF 1015 may directly be joined (fused) with the HNLF 1018. On this occasion, both are desirably polarization-maintaining fibers.

In this way, the laser output from the laser 10 is demultiplexed into the fundamental wave (1550 nm) and the second harmonic wave (780 nm) by the demultiplexer 11. The demultiplexer 11 includes a polarization beam splitter 1101, a PPLN (periodically poled lithium niobate) 1102, a dichroic mirror 1103, and a green cut filter 1104.

The beam splitter 1018 demultiplexes an incident beam into 50:50, and outputs one beam as the fundamental wave 1550 nm, and the other beam to the PPLN 1102. The PPLN 1102 has a periodic structure, and can convert the fundamental wave (1550 nm) to the second harmonic wave (780 nm). The second harmonic wave is output via the dichroic mirror 1103 and the green cut filter 1104.

Figure 4:
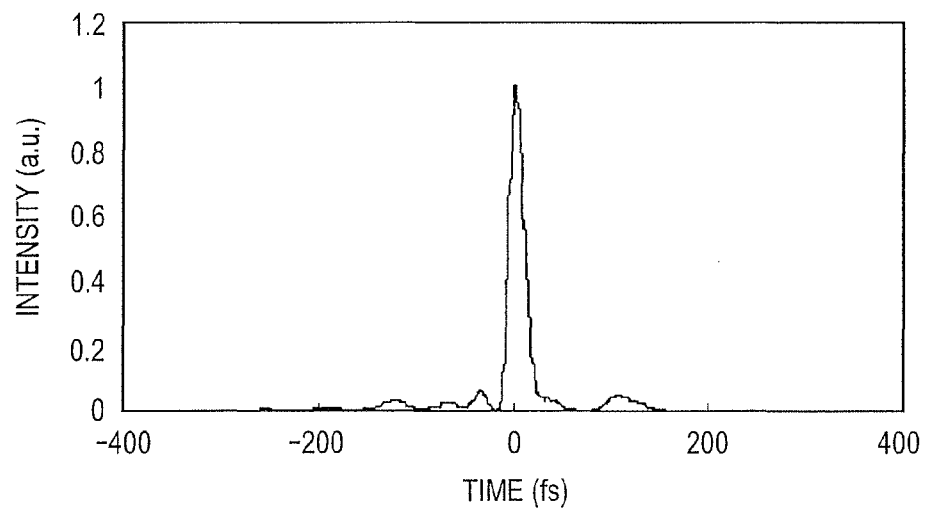
FIG. 4 is a wave form chart of a fundamental wave of a laser pulse according to the first embodiment of the present invention.
Figure 5:
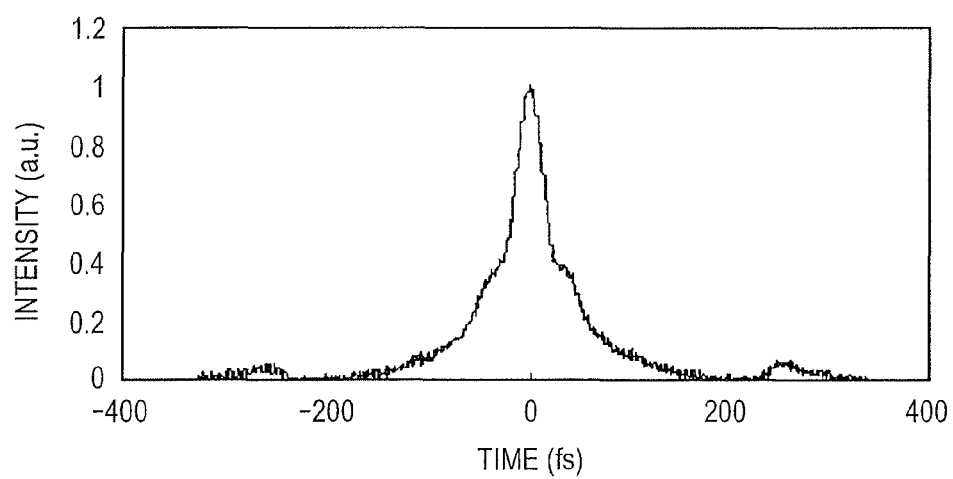
FIG. 5 is a wave form chart of a second harmonic wave of the laser pulse according to the first embodiment of the present invention.

FIGS. 4 and 5 show wave forms of the fundamental wave and the second harmonic wave having been demultiplexed by the demultiplexer 11. FIG. 4 shows the wave form of the fundamental wave, which has pulse width 17 fs and output 100 mW. FIG. 5 shows the wave form of the second harmonic wave, which has pulse width 37 fs, and output 10 mW.

(Diaphragm)

Figure 6:
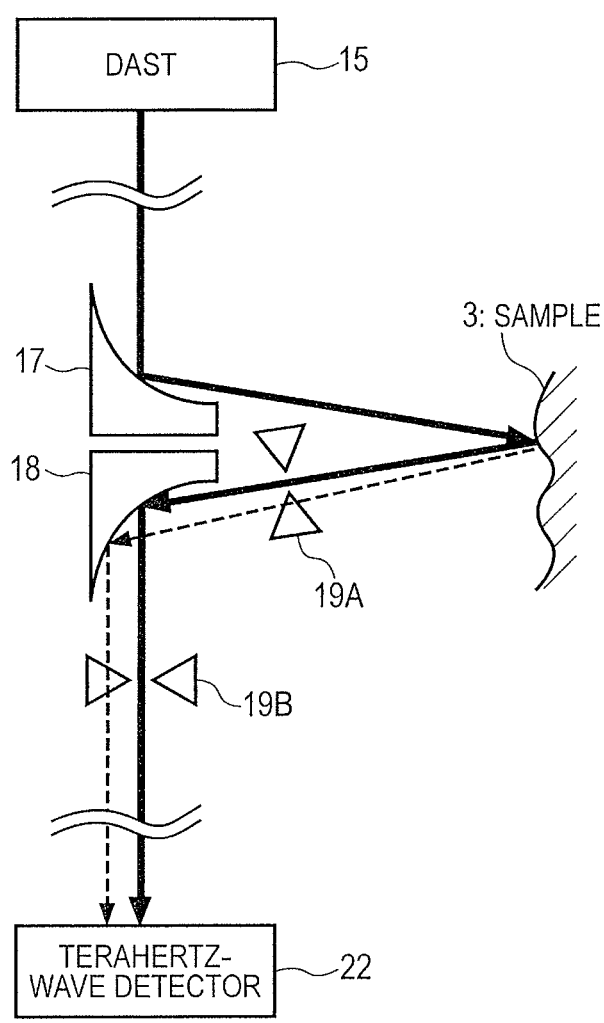
FIG. 6 is a drawing for explaining an optical path of reflected light according to the first embodiment of the present invention.

Subsequently, with reference to FIG. 6, the optical path of terahertz-waves reflected by the sample 3 will be explained. As described above, terahertz-waves irradiated from a terahertz-wave generation part such as the DAST 5 are reflected by the off-axis paraboloidal mirror 17 and arrive at the surface of the sample 3. The central part of the terahertz-wave is propagated through the path shown by a solid arrow as specular reflection. On the other hand, the peripheral part of the terahertz-wave is propagated through the path shown by a dotted arrow, differing from the specular reflection. The central part and peripheral part of the terahertz-wave are propagated differently due to the curved surface and irregularity such as island-shaped materials of the sample 3.

Generally, industrial products have various shapes, and are not necessarily configured with flat planes. Moreover, even when a coated film surface appears flat, actually, there exists difference of altitude caused by innumerable minute irregularities and island-shaped materials. When light having a prescribed beam diameter is irradiated on a coating film surface having difference of altitude, the difference of altitude is integrated and detected, and the film thickness can not be distinguished from the difference of altitude to make the detection of precise film thickness difficult.

Figure 21:
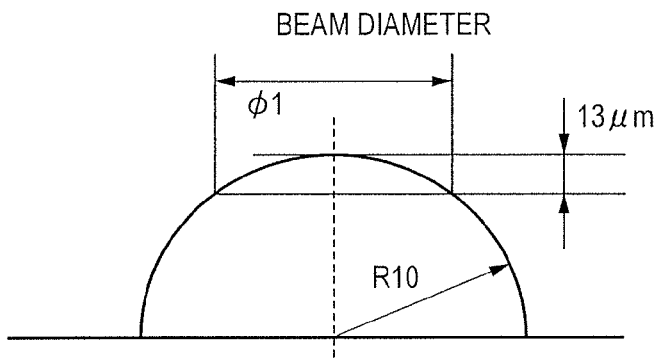
FIG. 21 is a drawing for explaining inspection of a coated film having a curved surface.

For example, suppose that, in the inspection apparatus described in Cited Document 1, a coating film having curvature 10 mm is irradiated with terahertz-waves having beam diameter 1 mm (see FIG. 21). On this occasion, the difference of altitude between the beam central part and peripheral part on the coating film is 13 μm, and precise measurement of film thickness not more than 13 μm becomes impossible. The point under discussion appears more notably when the film thickness becomes thinner.

Incidentally, it is possible to reduce the influence of difference of altitude of a curved surface by narrowing down the beam diameter as far as possible, but the beam diameter can not be narrowed down to not more than wavelengths, the diffraction limit of terahertz-waves.

In the embodiment, supposedly, when diaphragms 19A and 19B are not provided, not only specular reflection, but also reflected light of the periphery part of terahertz-waves is collimated by the off-axis paraboloidal mirror 18 and is condensed to the terahertz-wave detector 22. The reflection of a terahertz-wave periphery part has more time delay than the central part, and, therefore, if these are simultaneously converged to the terahertz-wave detector 22, detection resolution of film thickness lowers to make it impossible to measure a thin film precisely.

Figure 7:
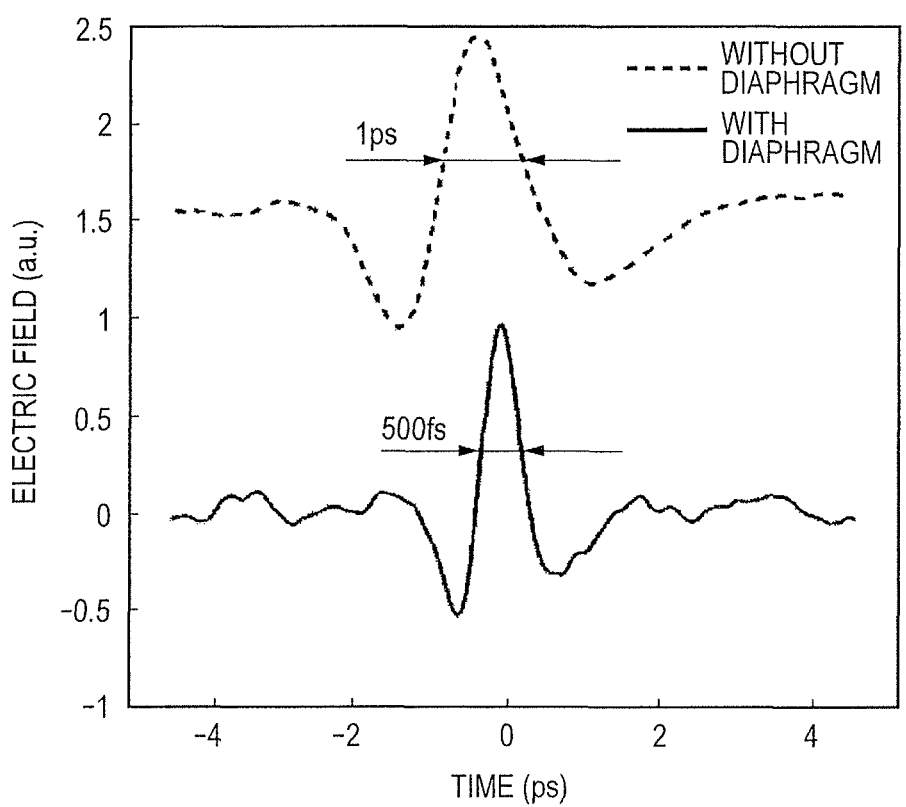
FIG. 7 is a wave form chart of reflected waves according to the first embodiment of the present invention.

For example, when diaphragms 19A and 19B are not provided, the pulse width of the detected terahertz-wave broadens to 1 ps (FIG. 7). It can be confirmed from FIG. 7 that the pulse width of the terahertz-wave becomes 500 fs by providing diaphragms 19A and 19B and the resolution in the time region is improved. Here, it may be considered to provide a diaphragm on the incident wave side, that is, between the off-axis paraboloidal mirror 17 and the sample 3. However, in this case, terahertz-waves can only be narrowed down to about the wavelength limit. Accordingly, as the embodiment, it is desirable to arrange diaphragms 19A and 19B on the reflected wave side. Incidentally, either one of the diaphragms 19A and 19B may be arranged.

In the embodiment, by arranging the diaphragms 19A and 19B to intercept reflected waves of the periphery part of terahertz-waves, it becomes possible to eliminate the component of terahertz-waves having time delay. According to such configuration, only specular reflection of terahertz-waves passes through openings of the diaphragms 19A and 19B to the terahertz-wave detector 22, and is detected by the terahertz-wave detector 22.

Incidentally, by arranging the diaphragms 19A and 19B on the optical path, the light volume might be reduced to deteriorate the SN ratio. In this case, the time constant at the time of detection of the lock-in amplifier 4 may be elongated, or the modulation frequency of the modulator 12 may be heightened to improve the SN ratio.

(Configuration of Control Unit)

Figure 8:
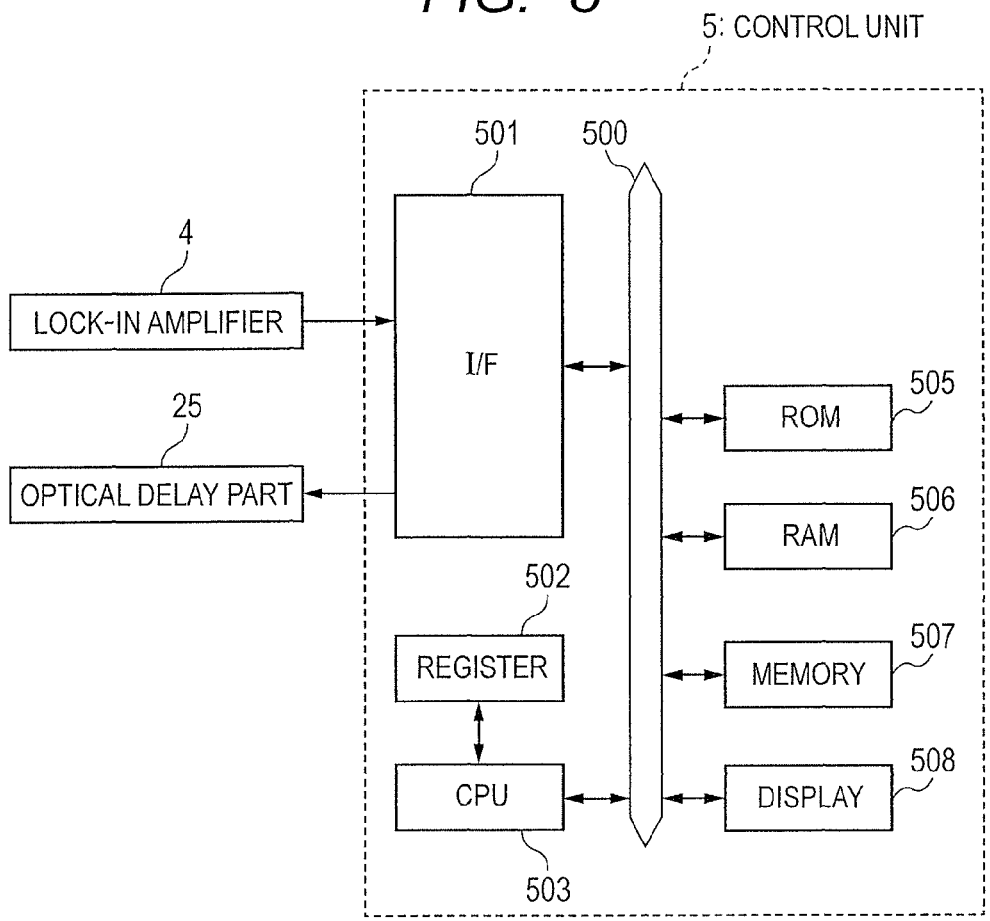
FIG. 8 is a block diagram of a control unit according to the first embodiment of the present invention.

FIG. 8 is the block diagram of the control unit 5 according to the embodiment. The control unit 5 is configured by a personal computer etc., and includes a data bus 500, an interface 501, a register 502, a CPU 503, a ROM 505, a RAM 507, a memory 508, a display 509 etc.

The data bus 500 is one for transferring data between the CPU 503 and respective parts such as the interface 501. The interface 501 is a port for inputting/outputting data. To the interface 501, the lock-in amplifier 4, an actuator 24, and the optical delay part 25 are connected. The control unit 5 can change the timing at which probe light arrives at the terahertz-wave detector 22 by controlling the position of movable mirror of the optical delay part 25.

The register 502 is a memory for temporarily storing data as a cash register for the operation of the CPU 503. The CPU 503 executes a previously determined inspection program to control the optical device 2 and analyze measured data.

The ROM 505 is used for storing basic programs of the control unit 5, such as BIOS. The RAM 506 is used as a work area for executing the inspection program. The external memory 507 is a hard disc drive, a CD drive, or a DVD drive, and is used for storing measured inspection data. The display 508 includes a liquid crystal display device, and is capable of showing graphically the wave form of terahertz-waves on the basis of inspection data, and of showing the film thickness, coating quality etc. of the sample 3.

(Measurement Principle of Film Thickness)

Figure 9:
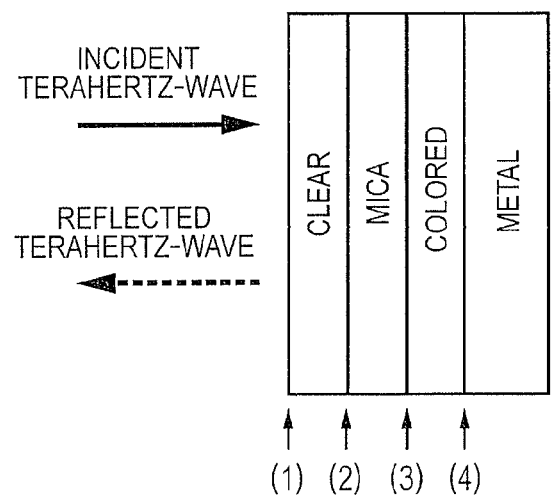
FIG. 9 is a cross-sectional view of a coated sample according to the first embodiment of the present invention.

Subsequently, the measurement principle of film thickness according to the embodiment will be described in detail. FIG. 9 is a cross-sectional view of a coated sample. The clear coating shown in the drawing is configured by forming a colored layer, a mica layer and a clear layer in order on metal that is a foundation. When terahertz-waves are irradiated, the terahertz-wave is reflected at a boundary surface where a refractive index changes. That is, the terahertz-wave is reflected at the boundary surface (1) of air and the clear layer, the boundary surface (2) of the clear layer and the mica layer, the boundary surface (3) of the mica layer and the colored layer, and the boundary surface (4) of the colored layer and the metal.

Figure 10:
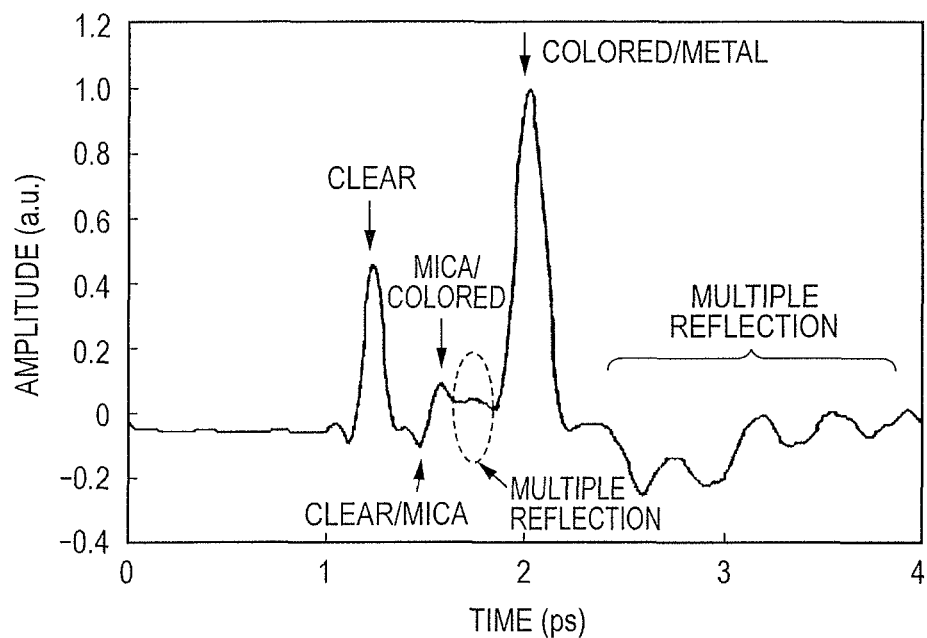
FIG. 10 is a wave form chart of reflected waves according to the first embodiment of the present invention.

FIG. 10 shows an example of reflected waves. In FIG. 10, the electric field intensity of the reflected waves is represented in a time region, wherein the horizontal axis shows a time axis, and the vertical axis shows amplitude. A positive peak that appears first in the time region of reflected waves shows the reflected wave at the boundary surface (1) of air and the clear layer. A negative peak that appears secondly shows the reflected wave at the boundary surface (2) of the clear layer and the mica layer. The reason why the peak shows a negative value is that the refractive index of the mica layer is smaller than the refractive index of the clear layer. A positive peak that appears thirdly shows the boundary surface (3) of the mica layer and the colored layer, and a positive peak that appears fourthly shows the reflected wave of the boundary surface (4) of the colored layer and the metal.

By substituting time differences between these peaks into Formula below, film thickness d can be calculated.

$$\text{Film thickness } d = \Delta t \cdot c \cdot \cos\theta / 2n \quad \text{Formula (1)}$$

Where, $\Delta t$ represents time difference, c represents the light velocity, $\theta$ represents an incident angle of a terahertz-wave, and n represents the refractive index of the coating.

Figure 11:
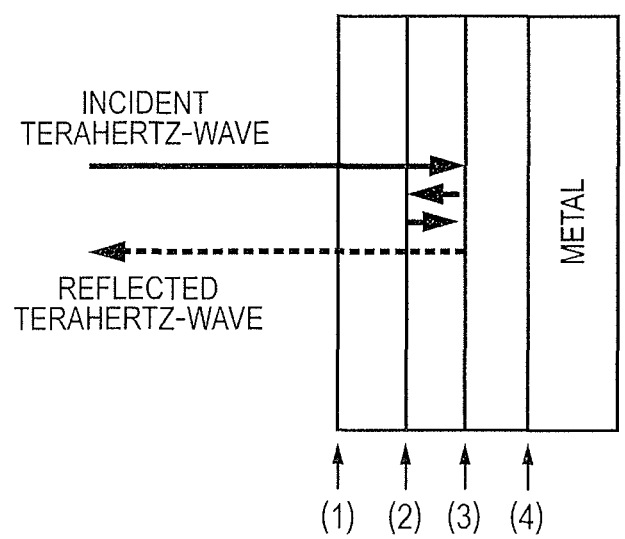
FIG. 11 is a drawing for explaining multiple reflection according to the first embodiment of the present invention.

In the wave form in FIG. 10, there exists a plurality of peaks caused by multiple reflection and noise, in addition to four peaks. For example, the existence of a small peak can be confirmed between the third and fourth peaks. This peak is caused, as shown in FIG. 11, by multiple reflection between boundary surfaces (2) and (3), that is, within the mica layer. A plurality of peaks that follows the fourth peak is caused by multiple reflection between boundary surfaces (3) and (4), or at another boundary surface. Accordingly, since these peaks are caused by multiple reflection, they can be neglected in the peak detection processing, and the peak detection processing may be performed between the first and fourth peaks. If the existence of two peaks between the first and fourth peaks is previously known, it is possible to avoid false detection of multiple reflection, noise etc. as a peak.

Figure 12:
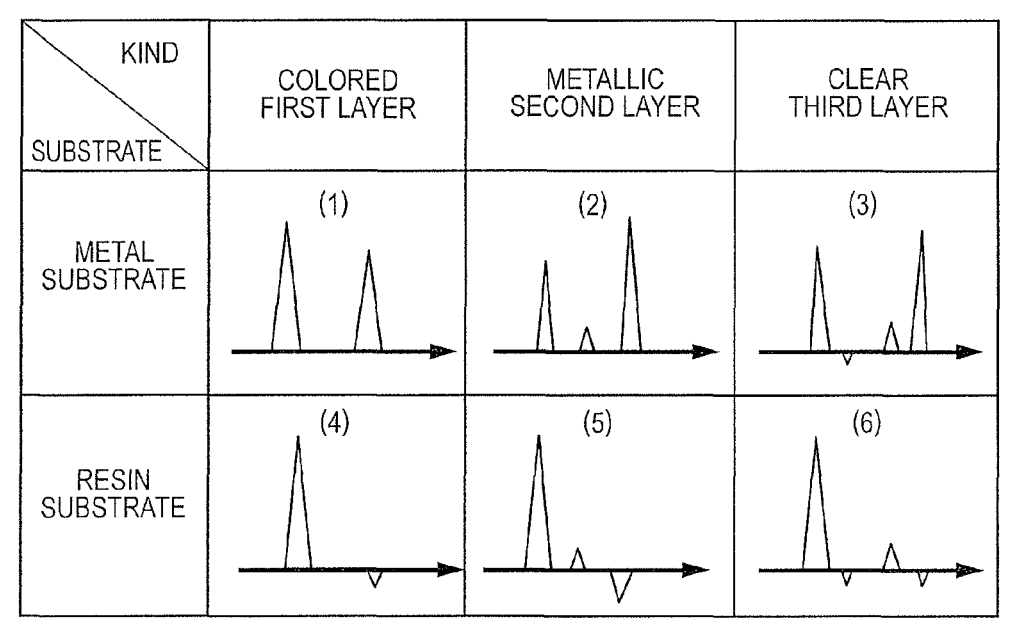

As described above, by making the control unit 5 store the peak pattern of the sample 3 to be a measurement object when extracting peaks from detected reflected waves, the peak corresponding to the boundary surface can be extracted precisely. FIG. 12 shows an example of the peak pattern. The peak pattern represents a theoretical value or an actual measured value of peaks of wave forms of various coatings.

In FIG. 12, the upper row shows the wave form of the sample 3 in which a coating film is formed on a metal substrate, and the lower row shows the wave form of the sample 3 in which a coating film is formed on a resin substrate. The left column shows a peak pattern of the first layer colored coating film, the central column shows a peak pattern of the second layer metallic coating film, and the right column shows a peak pattern of the third layer clear coating film, respectively. The first layer colored coating film is a coating film formed by applying a color paint on a substrate, the second layer metallic coating film is a coating film formed by applying a metallic paint and a clear paint in order over the substrate. The third clear coating film is a coating film formed by applying a color paint and a mica paint in order over the substrate.

The reflected wave at the boundary surface of coating films is determined by the reflectance at the boundary surface of two layers. Accordingly, when the reflectance is known, the intensity of the peak and the direction of the peak (positive peak, negative peak) appearing in the reflected wave can be guessed. Here, the reflectance can be calculated from refractive indices $n_1$ and $n_2$ of two layers according to Formula below.

$$(n_1 - n_2)/(n_1 + n_2) \quad \text{(Formula 2)}$$

Figures 18, 19, 20:
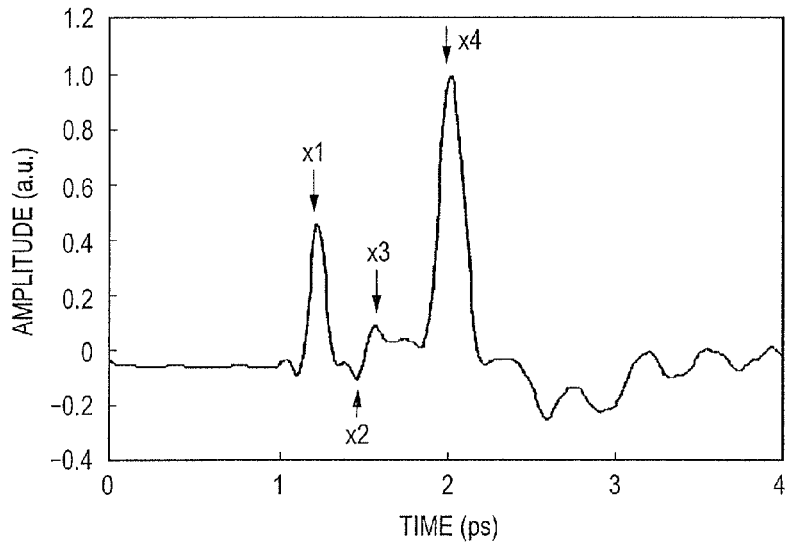
FIG. 18 is a wave form chart of reflected waves according to the first embodiment of the present invention.
FIG. 19 is a drawing for explaining a refractive index and thickness of a coated film according to the first embodiment of the present invention.
FIG. 20 is a drawing for explaining a measured refractive index of a coated film according to the first embodiment of the present invention.

For example, it is assumed that measured values of respective refractive indices of the color paint, the metallic paint, the clear paint, the mica paint and the ABS resin substrate are 2.1, 2.2, 1.8, 1.4, and 1.5 (FIG. 20). By substituting these refractive indices into the above Formula and calculating the reflectance at the boundary surface, it is possible to guess previously peak patterns 1 to 6 shown in FIG. 12. For example, it is guessed that the metal substrate and the third layer clear coating film give the peak pattern 3, in which four positive, negative, positive and positive peaks appear in order. The guessed value of intensity ratio of respective peaks is 3:1:2:8. In the resin substrate and the third layer clear coating film, the peak at the boundary surface of the coating film and the resin substrate becomes negative. Accordingly, this case gives the wave form pattern (6), in which four positive, negative, positive and negative peaks appear. Incidentally, these guessed values are obtained assuming that the coating film is sufficiently thin to such a degree that the decay of terahertz can be neglected. Incidentally, a peak pattern may be determined on the basis of actual measurement values.

When the range within which the film thickness can take (film thickness range) in the sample 3 is previously known, the time range between peaks appearing in the wave form may also be guessed. In the embodiment, as described later, by previously inputting the peak pattern and inputting guessed values of the film thickness range and intensity ratio range, it is possible to detect precisely only peaks corresponding to boundary surfaces from among innumerable peaks appearing in the wave form.

(Outline of Measurement Method)

Figure 13:
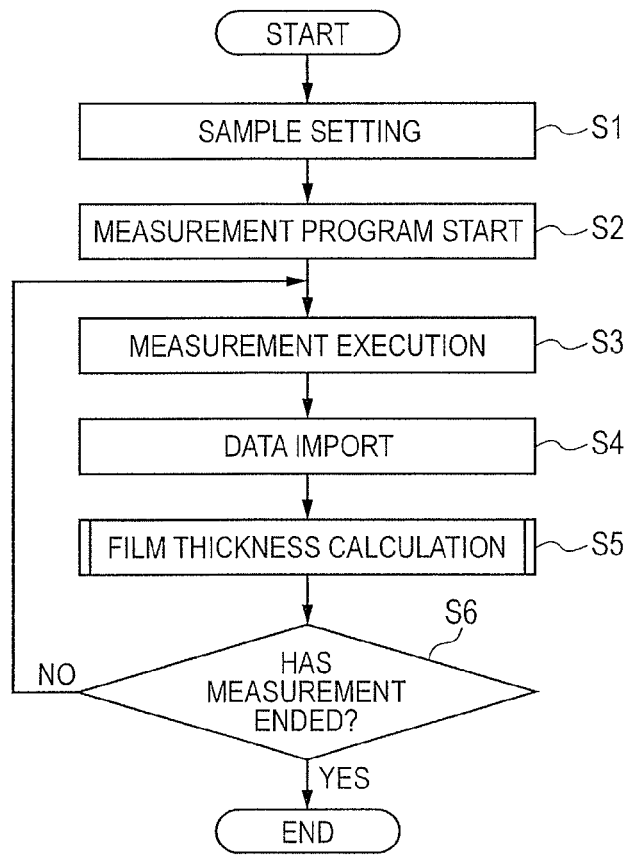
FIG. 13 is a flow chart representing an inspection method according to the first embodiment of the present invention.

Subsequently, with reference to the flow chart in FIG. 13, the inspection method according to the embodiment will be explained.

First, the sample 3 that is an inspection object is set to the optical device 3 (Step S1). On this occasion, the angle of the sample 3 relative to the optical device 2 is adjusted so that the terahertz-wave from the sample 3 passes through the diaphragms 19A and 19B. When an operator operates the control unit 5 to start the inspection program, the CPU 503 executes the inspection program stored in the external memory 506 to initialize the optical device 2, the lock-in amplifier 4 and the control unit 5 (Step S2).

Subsequently, the control unit 5 performs the measurement (Step S3). The light pulse of the femtosecond fiber laser 10 is separated into the fundamental wave of a 1550 nm component and the second harmonic wave of a 780 nm component, by the dichroic mirror 11. The fundamental wave enters the chopper 12, and the second harmonic wave enters the optical delay part 25. The chopper 12 modulates the fundamental wave at a prescribed modulation frequency, and the fundamental wave after the modulation is reflected by the mirror 13 and the paraboloidal mirror 14 for condensing the fundamental wave, and then is condensed to the DAST 15. The terahertz-wave generate by the DAST 15 is reflected by the off-axis paraboloidal mirrors 16 and 17, to be condensed to the sample 3.

The terahertz-wave reflected by the sample 3 passes through the opening part of the diaphragm 19A, and collimated by the off-axis paraboloidal mirror 18. Furthermore, the terahertz-wave passes through the opening part of the diaphragm 19B. In the embodiment, by arranging the diaphragms 19A and 19B, the reflected wave of periphery part of the terahertz-wave is interrupted. According to the configuration, only the specular reflection of terahertz-waves passes through the openings of diaphragms 19A and 19B to the terahertz-wave detector 22, and is detected by the terahertz-wave detector 22.

The terahertz-wave having passed through the diaphragm 19B is condensed to the terahertz-wave detector 22 by the off-axis paraboloidal mirror 20. Incidentally, the pulse of terahertz-waves is condensed repeatedly to the terahertz-wave detector 22 at the modulation frequency (1 kHz). On the other hand, the probe light having been delayed by a prescribed time by the optical delay part 25 is irradiated to the gap of the dipole antenna by the condenser lens 23. On this occasion, a minute electric current that is proportional to the electric field of terahertz-waves flows, and the minute electric current is detected synchronously by the lock-in amplifier 4. The lock-in amplifier 4 converts the amplified current to digital data by an A/D converter and records the same on a memory. Consequently, the intensity of the wave form of terahertz-waves at a prescribed timing is measured.

Figure 14:
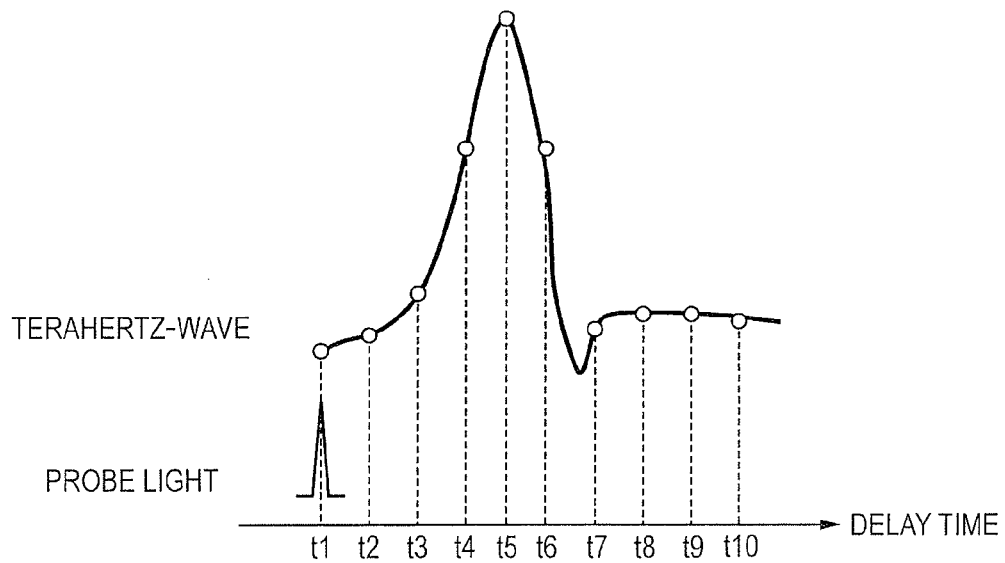
FIG. 14 is a drawing for explaining a sampling method of terahertz-waves according to the first embodiment of the present invention.

When sampling the wave form of terahertz-waves, the electric field intensity in the terahertz-wave detector 22 is measured, while shifting the timing of the probe light. That is, as shown in FIG. 14, the control unit 5 drives the movable mirror of the optical delay part 25 and sets the delay time of the prove light to be t1. The probe light is condensed to the terahertz-wave detector 22, and the electric field intensity of the terahertz-wave at the timing of delay time t1 is measured. Subsequently, the control unit 5 sets the delay time in the optical delay part 25 to be t2, and the electric field intensity of the terahertz-wave at this timing is detected by the terahertz-wave detector 22. In the same manner, delay times in the optical delay part 25 are changed in such an order as t3, t4, t5 . . . to enable the sampling of the wave form of terahertz-waves. The control unit 5 imports measured data showing the wave form of terahertz-waves, and stores the same on the memory 506 (Step S4).

The control unit 5 extracts peaks from the measured data, and calculates the film thickness (Step S5). The measurement result thus obtained is displayed on the display 508. When performing continuously the measurement after performing the above processing (YES in Step S6), the control unit 5 performs repeatedly the processing of Steps S4 to S5. On the other hand, when the measurement has terminated (No in Step S6), the control unit 5 terminates the processing.

(Film Thickness Calculation Processing)

Figure 15:
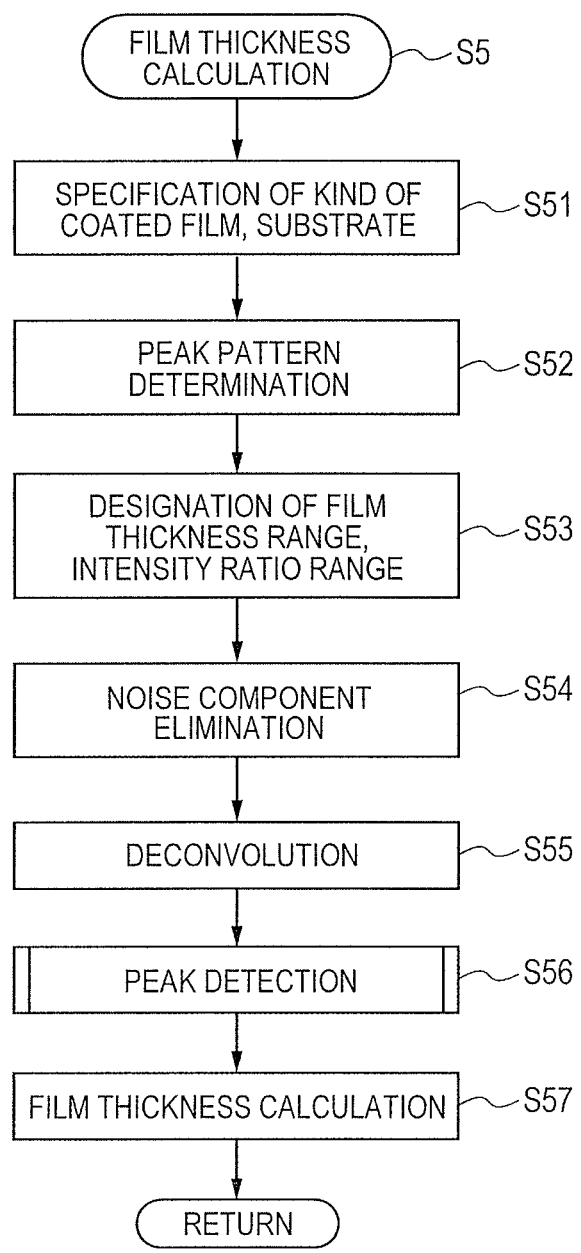
FIG. 15 is a flow chart of film thickness arithmetic processing according to the first embodiment of the present invention.

Subsequently, with reference to the flow chart in FIG. 15, the detail of the film thickness calculation processing (Step S5) will be explained.

In Step S51, an operator operates the control unit 5 to select and input one to be a measurement object from among the kinds of coating films and substrates displayed on the display 508. For example, from among the kinds shown in FIG. 12, the third layer clear coating film and the metal substrate are input. Consequently, the control unit 5 decides the peak pattern 3 shown in FIG. 12, and displays the same on the display 508 (Step S52).

Furthermore, the operator inputs the range of film thickness and the range of intensity ratio within which respective layers fall to the control unit 5 (Step S53). The range of film thickness of respective layers is determined by inputting the minimum value and the maximum value. For example, the minimum value 10 μm and the maximum value 100 μm of respective layers are input. In this case, the range of film thickness of the whole three layers is not less than 30 μm but not more than 300 μm.

The range of the intensity ratio is shown by the minimum value and the maximum value of the intensity ratio of each of peaks. For example, in a coating film having the refractive index shown in FIG. 20, the theoretical peak intensity is 3:1:2:8, according to Formula (2). It is possible to decide respective values of ⅕ and 5 times the theoretical intensity ratio as the minimum value and maximum value of the intensity ratio. Incidentally, the range of intensity ratio based on actual measurement values may be input.

The control unit 5 eliminates noise relative to the measured wave form data, using a frequency-dependent filter such as a low-pass filter (Step S54). After that, the control unit 5 furthermore eliminates noise components using a decombolution filter capable of eliminating only noise components (Step S55).

After extracting only signal components by these filtering processing, the control unit 5 detects peaks from the wave form data (Step S56). Furthermore, the control unit 5 substitutes the time difference between detected peaks into Formula (1) to calculate the film thickness (Step S57), and returns to the processing of the main flow chart in FIG. 13.

(Peak Detection Processing)

Figure 16:
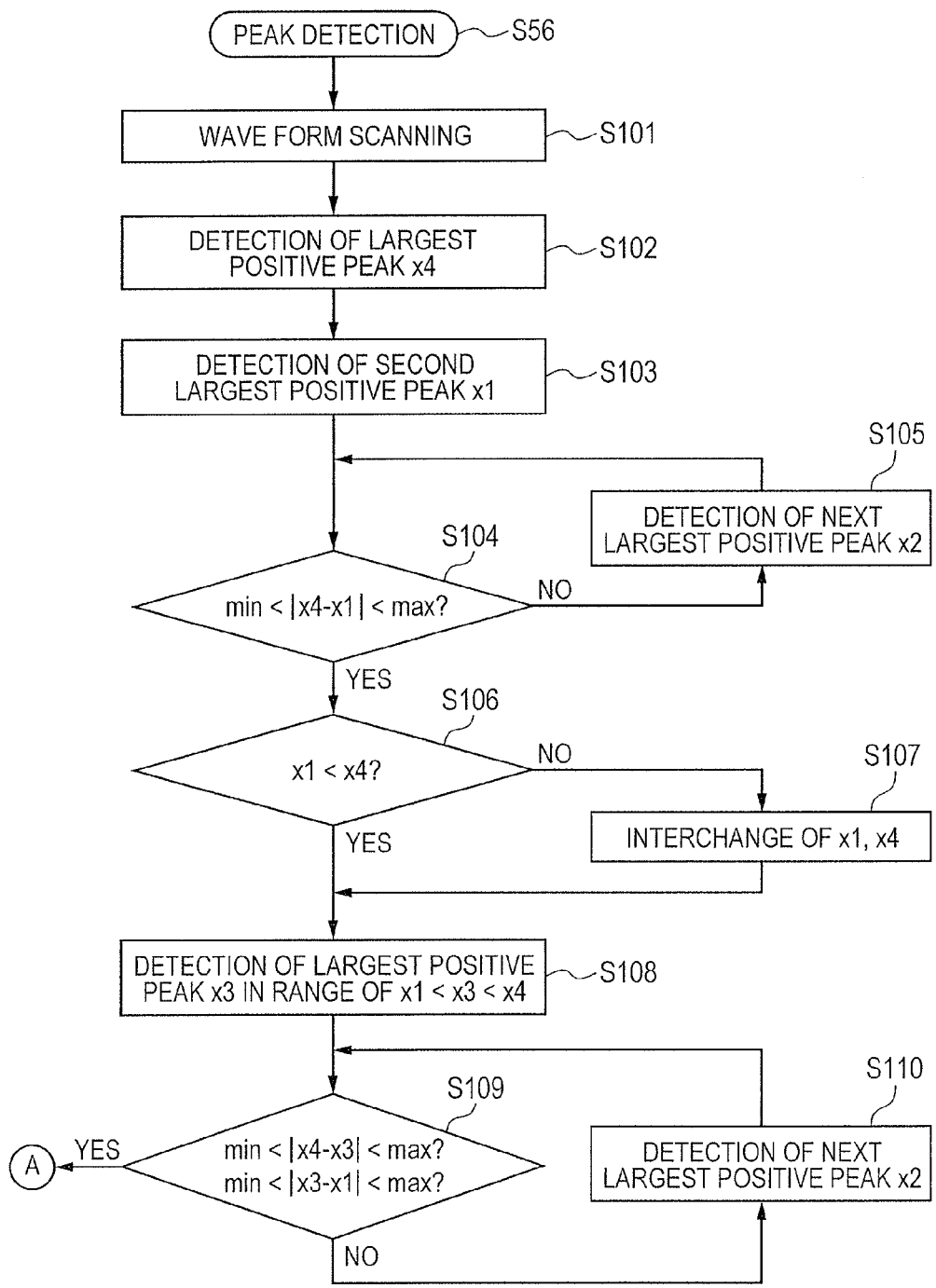
FIG. 16 is a flow chart of peak detection processing according to the first embodiment of the present invention.
Figure 17:
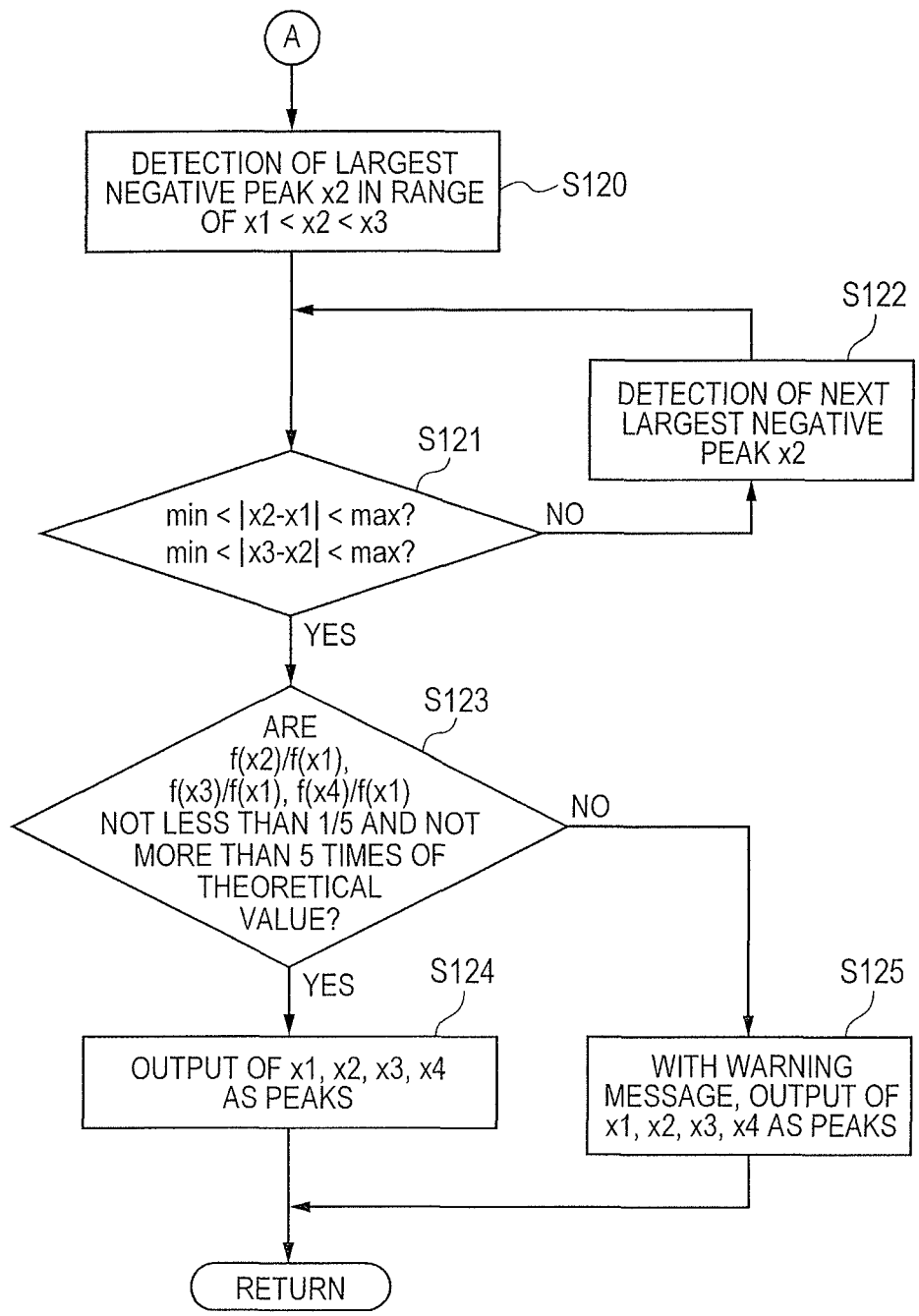
FIG. 17 is a flow chart of the peak detection processing according to the first embodiment of the present invention.

FIGS. 16 and 17 represent a flow chart showing the detail of peak detection processing (Step S56). In Step S53 in FIG. 15, the third layer clear coating film and metal substrate are selected as objects to be measured. Accordingly, the peak detection processing below is performed according to the peak pattern 3.

The control unit 5 scans the filtering-processed wave form data to detect the largest positive peak, and obtains time x4 corresponding to the peak (Step S102). The peak corresponds to the boundary surface (4) between the colored layer and the metal layer.

In the same manner, the control unit 5 obtains time x1 corresponding to the second largest positive peak on the basis of the peak pattern 3 (Step S103). The second largest peak corresponds to the boundary surface (1) of the air layer and the clear layer.

It is decided whether or not the absolute value of the difference between times x1 and x4 (film thickness) thus obtained falls in the previously determined film thickness range (Step S104). The film thickness range is input in Step S53, and corresponds to the minimum value and the maximum value that the thickness of the whole coating film may take. The film thickness of the whole layer input in Step S53 above is in a range of not less than 30 μm but not more than 300 μm.

When the absolute value of the difference between times x1 and x4 (film thickness) does not fall in the previously determined film thickness range (NO in Step S104), peaks may not have been detected correctly. Therefore, until the condition of Step S104 is satisfied, the detection of a next largest peak is performed (Step S105).

When the absolute value of the difference between times x1 and x4 (film thickness) is decided to fall in the previously determined film thickness range, the control unit 5 decides whether or not the time x4 is larger than the time x1 (Step S106). When the time x4 corresponds to the boundary surface (4) of the colored layer and the metal as shown in the peak pattern 3, the time x4 should be larger than the time x1. However, depending on the hue of the colored layer, the large and small of both peaks may be detected inversely. Accordingly, in this case, the times x1 and x4 are interchanged (Step S107).

Subsequently, the control unit detects the largest peak among positive peaks existing between times x1 and x4, and obtains time x3 of the peak (Step S108). Furthermore, the control unit 5 decides whether or not each of the absolute value of the difference between times x4 and x3 (thickness of the colored layer) and the absolute value of the difference between times x3 and x1 (thickness of the clear layer and the mica layer) falls in the previously determined film thickness range (Step S109).

When each film thickness does not fall in the previously determined film thickness range (NO in Step S109), peaks may not have been detected correctly. Therefore, until the condition in Step S109 is satisfied, a next largest peak is detected (Step S110).

When each film thickness falls in the previously determined film thickness range (YES in Step S109), according to the peak pattern 3, the control unit 5 detects time x2 of a negative peak existing between times x1 and x3 (Step S120). The negative peak corresponds to the boundary surface (2) of the clear layer and the mica layer.

In Step S121, the control unit 5 decides whether or not each of the absolute value of the difference between times x2 and x1 (thickness of the clear layer) and the absolute value of the difference between times x3 and x2 (thickness of the colored layer) falls in the previously determined film thickness range.

When each film thickness does not fall in the previously determined range (NO in Step S121), peaks may not have been detected correctly. Therefore, until the condition in Step S121 is satisfied, a next largest negative peak is detected (Step S122).

Subsequently, the control unit 5 decides whether or not the intensity ratios of respective peak values $f(x1)/f(x4)$, $f(x2)/f(x4)$ and $f(x3)/f(x4)$ fall in the previously determined intensity ratio range (Step S123). The intensity ratio range has been input in step S63 above, and, for example, is a range of not less than 1/5 but not more than 5 times the theoretical value.

In the wave form shown in FIG. 18, the theoretical value of the intensity ratio of $f(x1)$, $f(x2)$, $f(x3)$ and $f(x4)$ is 9:1:3:11. The intensity ratio in the measured wave form is 0.88:0.13: 0.25:1.00, which falls in the designated intensity ratio range. Incidentally, when wave form data is normalized so that $f(x4)$ becomes 1, $f(x2)/f(x4)$, $f(x3)/f(x4)$ and $f(x4)/f(x4)$ become equal to $f(x2)$, $f(x3)$ and $f(x4)$, respectively.

When the condition of Step S123 is satisfied, the control unit outputs times x1, x2, x3 and x4 to the display 508 (Step S124). When the condition of Step S123 is not satisfied, a measurement error may have occurred. Therefore, the control unit 5 outputs times x1, x2, x3 and x4 to the display 508 with warning (Step S125).

FIG. 19 shows the measurement result calculated by the above processing. As shown in the left column, the sample 3 is a coating film including the first layer (clear layer) 20 μm, the second layer (mica layer) 10 μm, and the third layer (colored layer) 30 μm. According to the previous measurement result, respective refractive indices were 1.8, 1.5, and 2.1. As the result of actual measurement of the sample 3, the delay time of reflected waves by the first layer was 220 fs, the delay time of reflected waves by the second layer was 100 fs, and the delay time of reflected waves by the third layer was 440 fs. The substitution of these measurement results in Formula (1) gave the thickness of the first layer 18 μm, the thickness of the second layer 10 μm, and the thickness of the third layer 31 μm. Incidentally, the intersection in the measurement result of the film thickness is ±2 μm. From the measurement result, it can be confirmed that extremely precise film thickness measurement was performed.

As described above, according to the embodiment, by detecting a plurality of peaks from wave form data according to the previously input peak pattern, it is possible to avoid false detection of multiple reflection, noise etc. as a peak. In addition, by detecting peaks in the descending order of amplitude in the wave form data, it is possible to avoid false detection of multiple reflection, noise etc. as a peak. Furthermore, by previously inputting the film thickness range and the intensity ratio range of the sample to be a measurement object, the measurement error due to false detection of peaks can be prevented.

Second Embodiment

Subsequently, the inspection apparatus according to the second embodiment of the present invention will be explained. The inspection apparatus according to the embodiment is a modified example of the first embodiment, which enables measuring the film thickness of a metallic coating. The configuration of the inspection apparatus according to the embodiment is approximately the same as that in the first embodiment, except for the peak detection processing (Step S56). Therefore, a different configuration will be explained.

Figure 22:
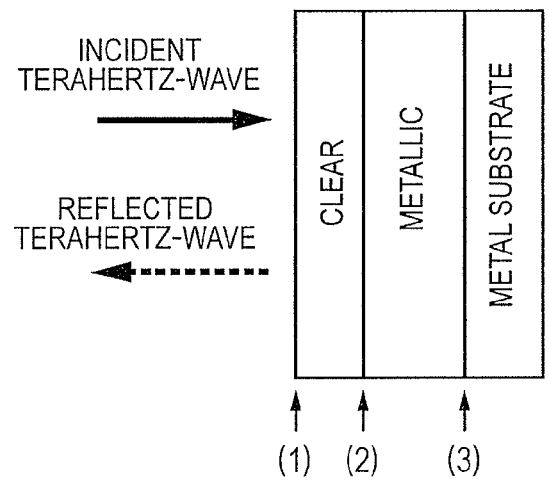
FIG. 22 is a cross-sectional view of a metallic coated sample according to a second embodiment of the present invention.

FIG. 22 is the cross-sectional view of the metallic coated sample. As shown in the drawing, the metallic coating is configured by forming the metallic layer and the clear layer in the order over metal that is a foundation. When terahertz-waves are irradiated to the coated sample, the terahertz-wave is reflected by the boundary surface where the refractive index changes. That is, the terahertz-wave is reflected at the boundary surface (1) of air and the clear layer, at the boundary surface (2) of the clear layer and the metallic layer, and at the boundary surface (3) of the metallic layer and metal.

Figure 23:
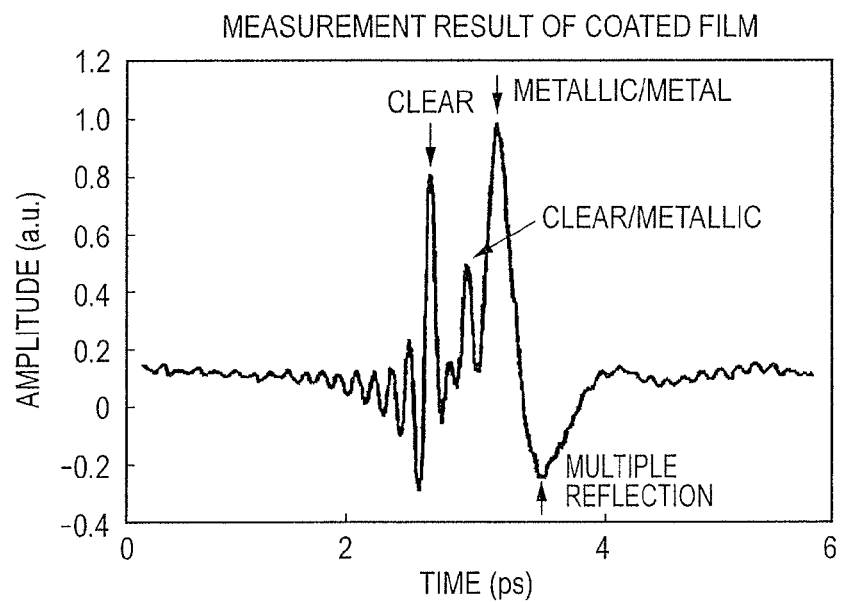
FIG. 23 is a wave form chart of reflected waves according to the second embodiment of the present invention.

FIG. 23 shows the electric field intensity of reflected waves in a time region, wherein the horizontal axis shows a time axis and the vertical axis shows amplitude. The positive peak that appears first in the time region of reflected waves shows the reflected wave at the boundary surface (1) of air and the clear layer. The positive peak that appears secondly shows the reflected wave at the boundary surface (2) of the clear layer and the metallic layer. The positive peak that appears thirdly shows the reflected wave at the boundary surface (3) of the metallic layer and metal. The peak subsequent to the third peak is caused by multiple reflection.

In the embodiment, too, in the same manner as in the first embodiment, peaks corresponding to boundary surfaces can precisely extracted by making the control unit 5 store the peak pattern of the sample 3 to be the measurement object when extracting peaks from detected reflected waves. For example, when respective measured values of refractive indices of clear paint and metallic paint are 1.8 and 2.2, a guessed value of the intensity ratio of peaks derived from refractive indices is approximately 3:1:10.

When the range that the film thickness in the sample 3 can take (film thickness range) is previously known, the time range between peaks that appear in the wave form may also be guessed. In the embodiment, as described later, by previously inputting the peak pattern and inputting guessed values of the film thickness range and intensity ratio range, it is possible to detect precisely only peaks corresponding to boundary surfaces from among innumerable peaks appearing in the wave form.

Figure 24:
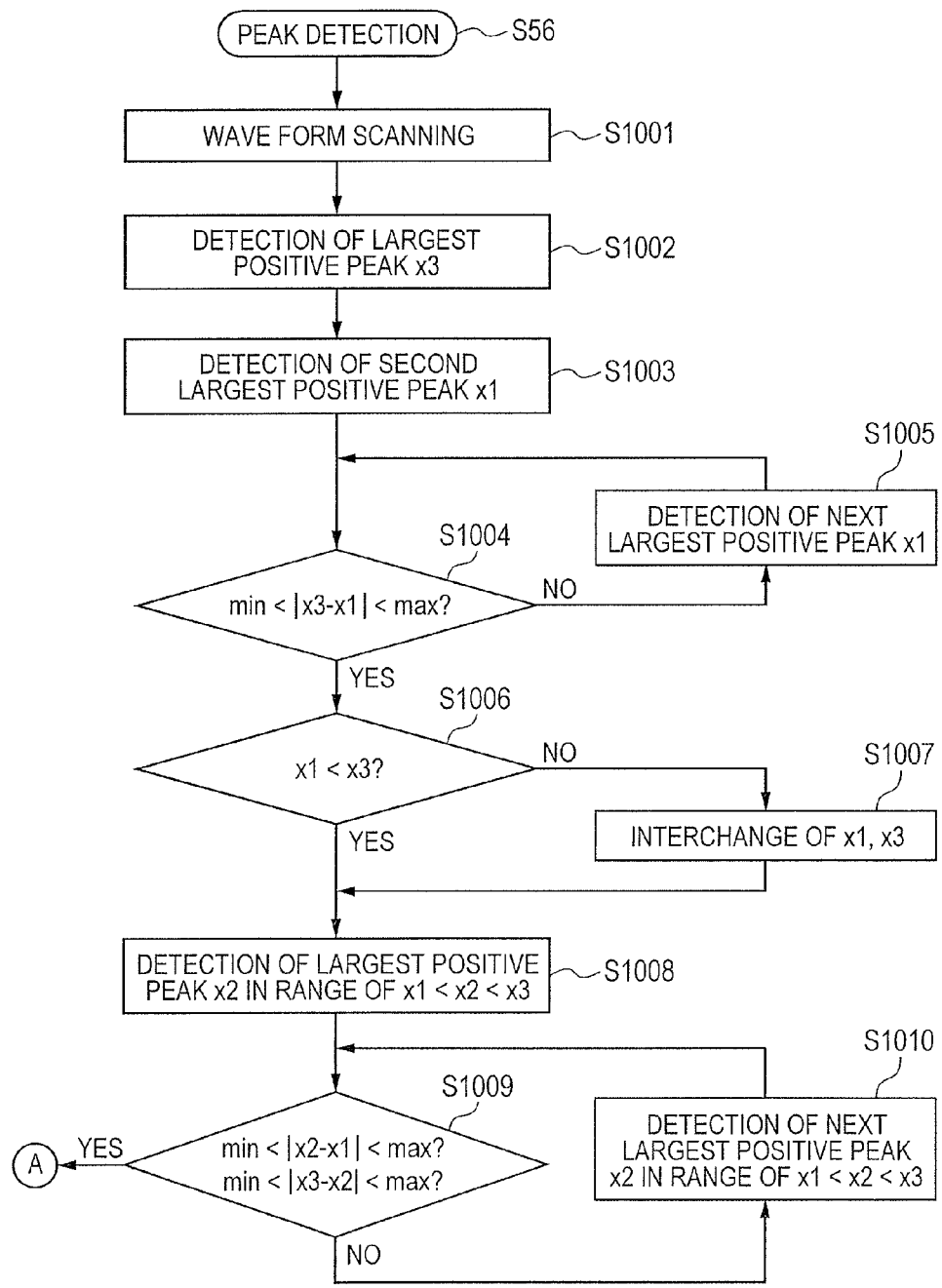
FIG. 24 is a flow chart of peak detection processing according to the second embodiment of the present invention.
Figure 25:
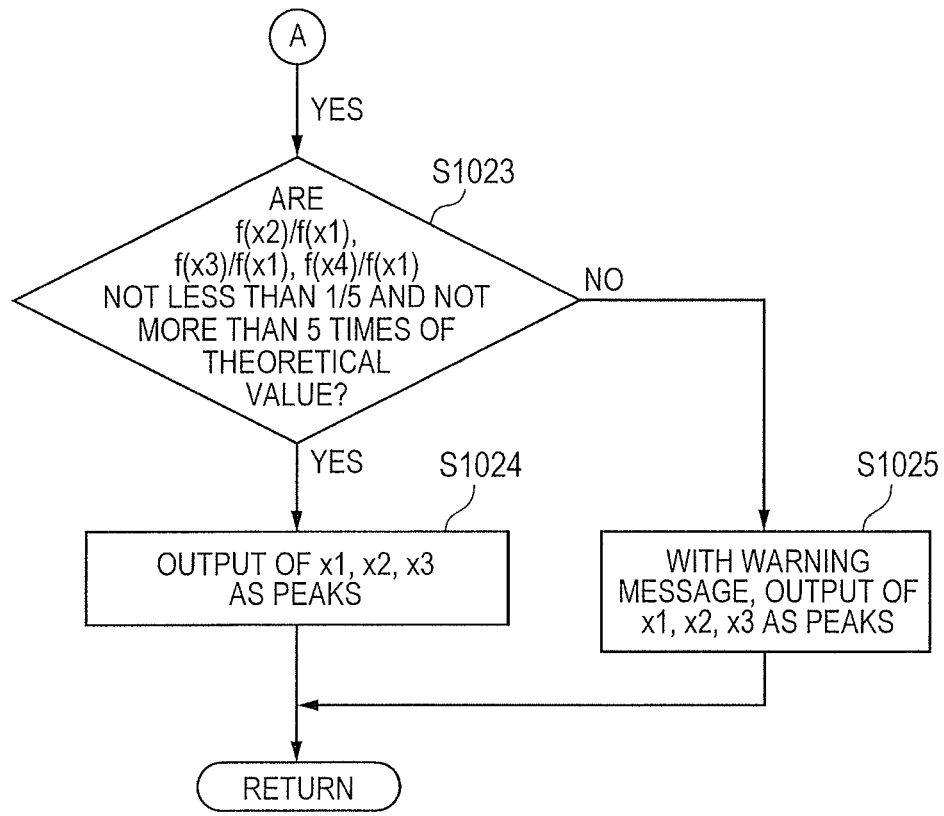
FIG. 25 is a flow chart of the peak detection processing according to the second embodiment of the present invention.

Subsequently, with reference to the flow chart in FIGS. 24 and 25, the detail of the peak detection processing according to the embodiment will be explained. The peak detection processing is performed in the film thickness calculation processing (FIG. 15) relative to wave form data measured by measurement processing (FIG. 13), in the same manner as in the first embodiment. In Step S53 in FIG. 15, the metallic second layer coating film and the metal substrate are selected as measurement objects. Accordingly, the peak detection processing below is performed according to the peak pattern 2.

The control unit 5 scans the filtering-processed wave form data (Step S1001) to detect the largest positive peak, and obtains time X3 corresponding to the peak (Step S1002). The peak corresponds to the boundary surface (3) of the metallic and metal layers.

In the same manner, the control unit 5 obtains the time x1 corresponding to the second largest positive peak on the basis of the peak pattern 2 (Step S1003). The second largest peak corresponds to the boundary surface (1) of the air layer and the clear layer.

It is decided whether or not the absolute value of the difference between times x1 and x3 thus obtained (film thickness) falls in the previously determined film thickness range (Step S1004). The film thickness range is input in Step S53, and corresponds to the minimum value and the maximum value that the thickness of the whole coating film can take.

When the absolute value of the difference between times x1 and x3 (film thickness) does not fall in the previously determined film thickness range (NO in Step S1004), peaks may not have been detected correctly. Therefore, until the condition in Step S1004 is satisfied, a next largest peak is detected (Step S1005).

When the absolute value of the difference between times x1 and x3 (film thickness) is decided to fall in the previously determined film thickness range, the control unit 5 decides whether the time x3 is larger than the time x1 or not (Step S1006). When the time x3 corresponds to the boundary surface (3) of the metallic layer and metal as shown in the peak pattern 2, the time x3 should be larger than the time x1. However, depending on the composition of the metallic layer, the large and small of both peaks may be detected inversely. Accordingly, in this case, the times x1 and x3 are interchanged (Step S1007).

Subsequently, the control unit 5 detects the largest peak among positive peaks existing between times x1 and x3, and obtains time x2 of the peak (Step S1008). Furthermore, the control unit 5 decides whether or not each of the absolute value of the difference between times x2 and x1 (thickness of the clear layer) and the absolute value of the difference between times x3 and x2 (thickness of the metallic layer) falls in the previously determined film thickness range (Step S1009).

When each film thickness does not fall in the previously determined film thickness range (NO in Step S1009), peaks may not have been detected correctly. Therefore, until the condition in Step S1009 is satisfied, a next largest peak is detected (Step S1010).

When each film thickness falls in the previously determined film thickness range (YES in Step S1009), the control unit 5 decides whether or not the intensity ratios of respective peak values $f(x2)/f(x1)$ and $f(x3)/f(x1)$ fall in the previously determined intensity ratio range (Step S1023). The intensity ratio range has been input in step S63 above, and, for example, is a range of not less than $\frac{1}{5}$ but not more than 5 times the theoretical value.

When the condition of Step S1023 is satisfied, the control unit 5 outputs times x1, x2 and x3 to the display 508 (Step S1024). When the condition of Step S1023 is not satisfied, a measurement error may have occurred. Therefore, the control unit 5 outputs times x1, x2 and x3 to the display 508 with warning (Step S1025).

As described above, also in the embodiment, by detecting a plurality of peaks from wave form data according to the previously input peak pattern, it is possible to avoid false detection of multiple reflection, noise etc. as a peak. In addition, by detecting peaks in the descending order of amplitude in the wave form data, it is possible to avoid false detection of multiple reflection, noise etc. as a peak. Furthermore, by previously inputting the film thickness range and the intensity ratio range of the sample to be a measurement object, the measurement error due to false detection of peaks can be prevented.

In the metallic coating, there is such a case as to apply a primer on the substrate to improve acoustic absorption of a metallic paint to the substrate. Since terahertz-waves are also capable of passing through the primer, the film thickness can be measured while considering that the primer is also one coating film. In the embodiment, the measurement of the second and third layers are mentioned, but the film thickness measurement is possible for a single layer film, needless to say, and for coating films of not less than four layers according to a similar idea.

Third Embodiment

Figure 26:
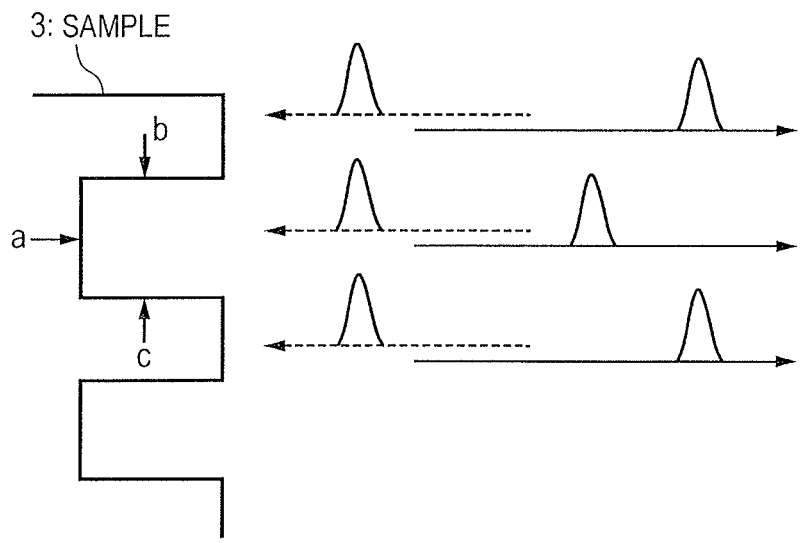
FIG. 26 is a drawing for explaining a coated film inspection apparatus according to a third embodiment of the present invention.
Figure 27:
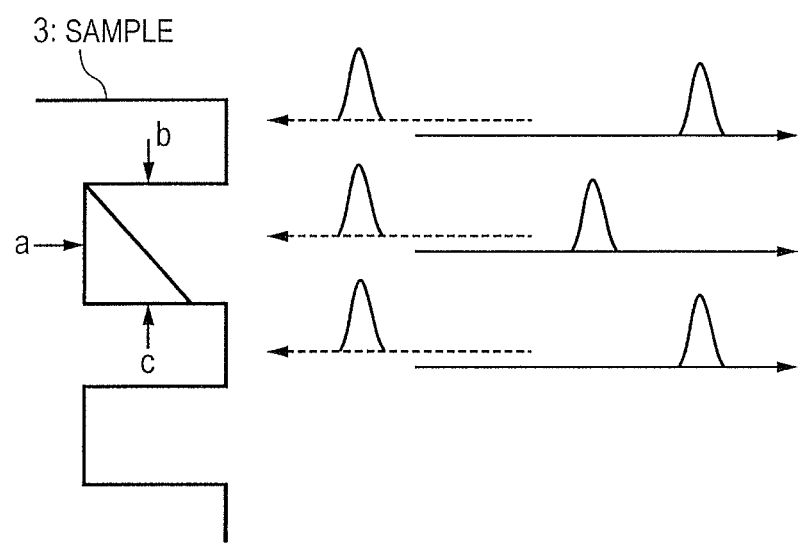
FIG. 27 is a drawing for explaining the coated film inspection apparatus according to the third embodiment of the present invention.

FIGS. 26 and 27 are drawings for explaining the inspection apparatus according to the third embodiment of the present invention. According to the above-mentioned inspection apparatus according to the first embodiment, as shown in FIG. 26, even in a case where a trench exists in the sample 3, terahertz-waves are not scattered but arrive at the terahertz-wave detector 22. Accordingly, by measuring the delay of reflected waves, the film thickness of a bottom part a of the trench can be obtained. However, film thicknesses in wall parts b and c to which terahertz-waves are not irradiated can not be measured. In piston cylinders, the preciseness of a coating given to the inside has a large influence on engine performance, and, therefore, the necessity for measuring the wall part is high.

The inspection apparatus according to the embodiment has a reflector 301 that may be put in the trench, in addition to the inspection apparatus according to the first embodiment (FIG. 27). The reflector 301 may be of any kind if it can reflect terahertz-waves, including a prism etc. After being reflected at the reflector 301, the terahertz-wave is irradiated to the wall part b, and the reflected wave from the wall b is detected by the terahertz-wave detector 22 via the reflector 301. Accordingly, it becomes possible, for example, to detect a coating film given to the inside of a piston.

Since the other configuration according to the embodiment is the same as that according to the first embodiment, the explanation thereof is omitted.

Fourth Embodiment

Subsequently, an inspection apparatus 1a of a coating film according to the fourth embodiment of the present invention will be explained. The inspection apparatus 1a is able to perform the measurement of the orientation state of the metallic coating, at the same time as the measurement of the film thickness.

(Overall Configuration)

Figure 28:
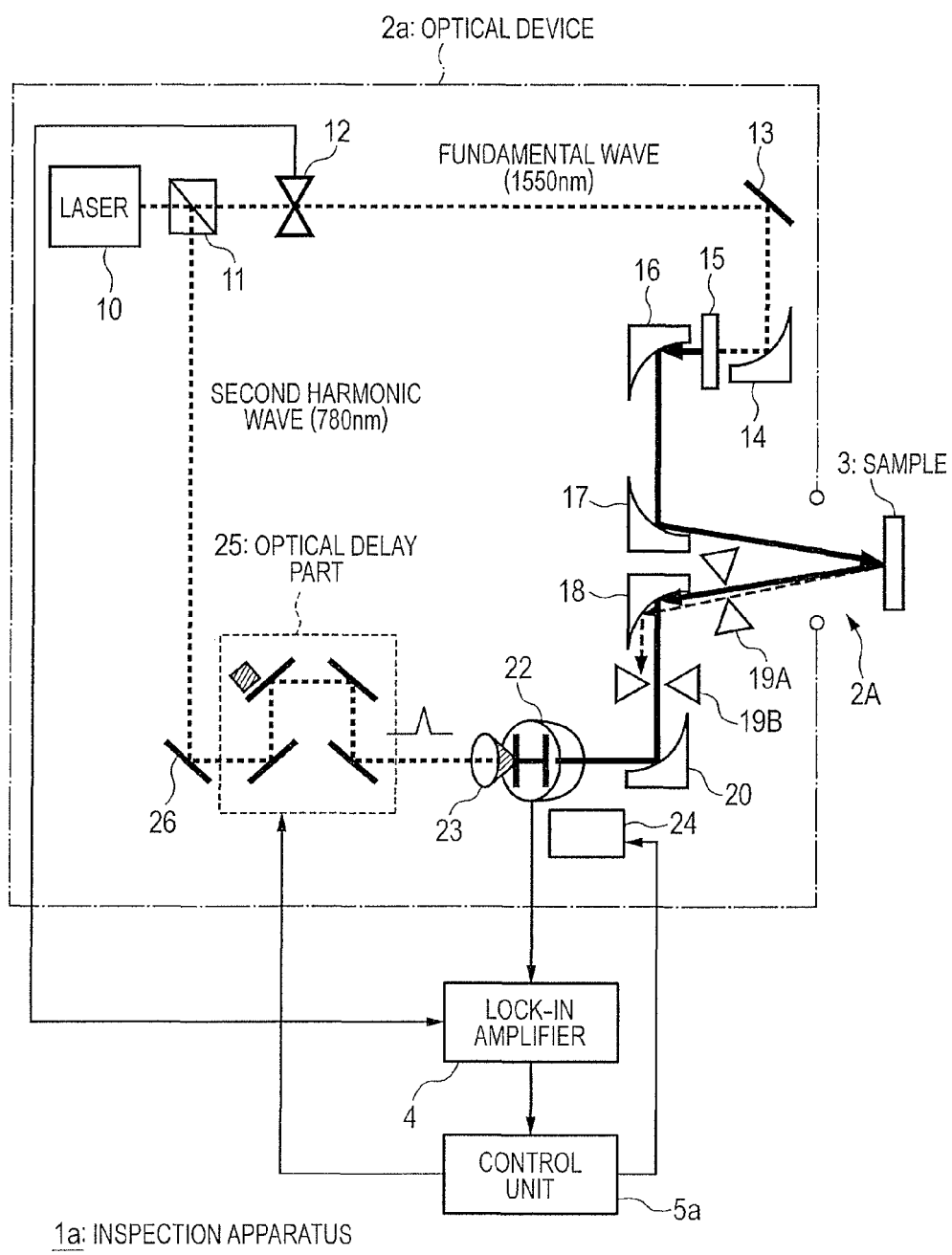
FIG. 28 is a block diagram of a coated film inspection apparatus according to a fourth embodiment of the present invention.

FIG. 28 is the block diagram of the coating film inspection apparatus according to the fourth embodiment of the present invention. The apparatus includes an optical device 2a that irradiates terahertz-waves to the sample 3 and detects reflected waves, the lock-in amplifier 4 that amplifies synchronously the detection signal of reflected waves, and a control unit 5a that controls the inspection apparatus. In FIG. 28, members to which the same reference numeral as that in FIG. 1 is given are configured in the same manner as members according to the first embodiment. Hereinafter, with priority given to points different from the configuration according to the first embodiment, the configuration according to the fourth embodiment will be explained.

(Configuration of Optical Device)

The optical device 2a includes the femtosecond fiber laser 10, the dichroic mirror 11, the chopper 12, the mirror 13, the paraboloidal mirror 14 for condensing the fundamental wave, the DAST 15, off-axis paraboloidal mirrors 16, 17, 18 and 20, the diaphragm 19, the terahertz-wave detector 22, the condenser lens 23, the actuator 24, the optical delay part 25, and the mirror 26. The optical device 2 is sealed from the outside by a housing, and the inside of the housing is desirably dehumidified, filled with nitrogen gas, or evacuated. The configuration can prevent terahertz-waves from being absorbed by moisture in air.

The optical device 2a according to the embodiment has the actuator 24, in addition to the configuration of the first embodiment. The actuator 24 is configured by a stepping motor etc., and has such function as rotating a terahertz-wave detector 22 around the light axis by a prescribed angle. Here, it is considered to select two polarization axes perpendicular to each other, but, for phase matching conditions of the DAST 15, the terahertz-wave has linear polarization. Consequently, when the polarization axis is rotated in 90°, the detection of terahertz-waves by a dipole antenna of the terahertz-wave detector 22 becomes difficult. In the embodiment, by rotating the terahertz-wave detector 22 in 45°, horizontally polarized light (polarization component perpendicular to gravity) and polarized light of 45° relative to the horizontally polarized light are detected by the terahertz-wave detector 22.

The actuator 24 may include an adjustment mechanism not only for the rotation angle of the terahertz-wave detector 22 but also for an alignment. When the terahertz-wave detector 22 of the dipole antenna is used, it is necessary to condensate terahertz-waves to the antenna gap. When the alignment is shifted by rotating the terahertz-wave detector 22, the actuator 24 may perform alignment adjustment.

The control unit 5a is configured, for example, by a personal computer, and synchronizes the chopper 12, the optical delay part 23 and the lock-in amplifier 4 at the modulation frequency. And, the control unit 5 may analyze measured data from the lock-in amplifier 4 to decide whether the flake orientation of the metallic coating that is a metallic coated sample is good or bad.

(Configuration of Control Unit)

Figure 29:
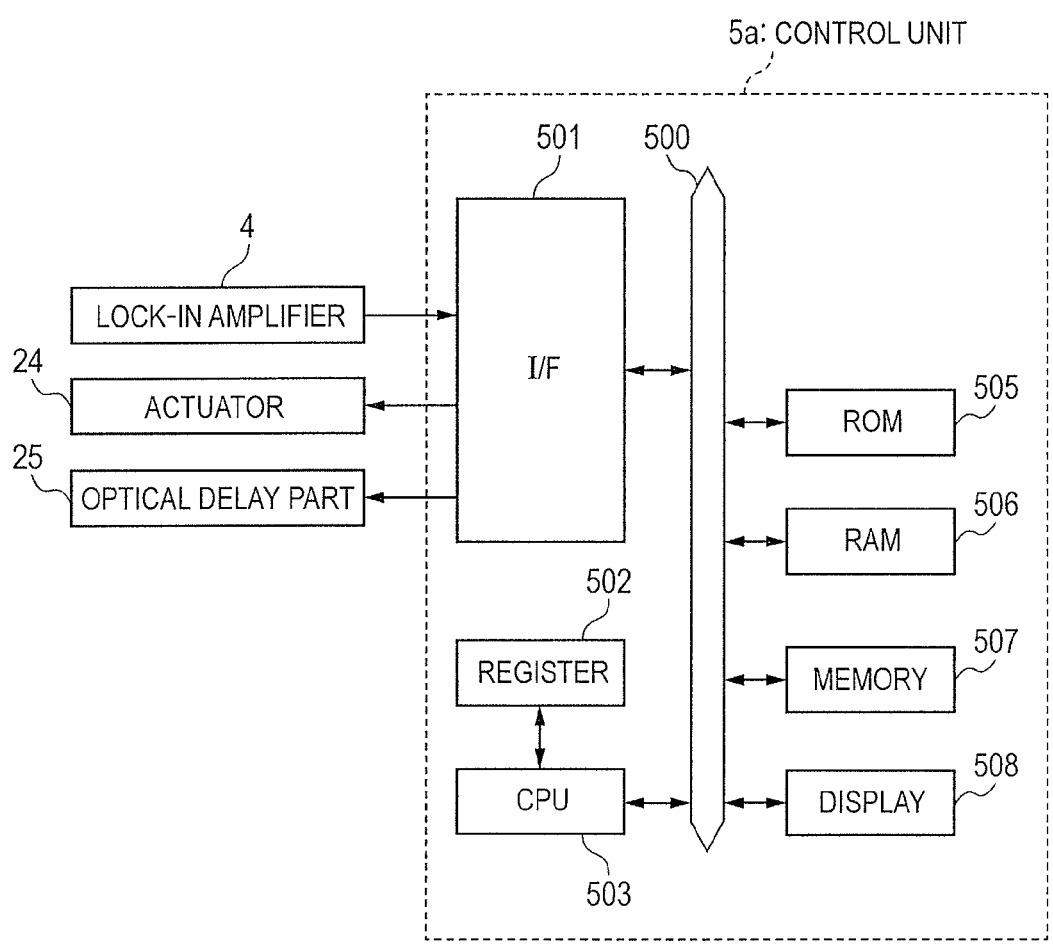
FIG. 29 is a block diagram of a control unit according to the fourth embodiment of the present invention.

FIG. 29 is the block diagram of the control unit 5a according to the embodiment. The control unit 5a is configured by a personal computer etc., and includes the data bus 500, the interface 501, the register 502, the CPU 503, the ROM 505, the RAM 507, the memory 508, the display 509 etc.

The data bus 500 is one for performing data transfer between the CPU 503 and respective parts such as the interface 501. The interface 501 is a port for input/output of data. To the interface 501, the lock-in amplifier 4, the actuator 24, and the optical delay part 25 are connected. The control unit 5 can change the timing at which the probe light arrives at the terahertz-wave detector 22, by controlling the position of the movable mirror of the optical delay part 25. And, the control unit 5 makes the terahertz-wave detector 22 rotate automatically by controlling the actuator 24, and two kinds of polarization components different in angles are detected by the terahertz-wave detector 22.

The register 502 is a memory for temporarily storing data as a cache register for the operation of the CPU 503. The CPU 503 executes a previously determined inspection program to control the optical device 2, and performs the analysis of measured data.

The ROM 505 is used for storing base programs such as BIOS of the control unit 5a. The RAM 506 is used as a work area for executing an inspection program. The external memory 507 is a hard disc drive, a CD drive or a DVD drive, and is used for the storage of measured inspection data. The display 508 includes a liquid crystal display device, which represents graphically the wave form of terahertz-waves on the basis of inspection data, and may display good or bad of the orientation of flakes in a metallic coating.

(Inspection Method)

Figure 30:
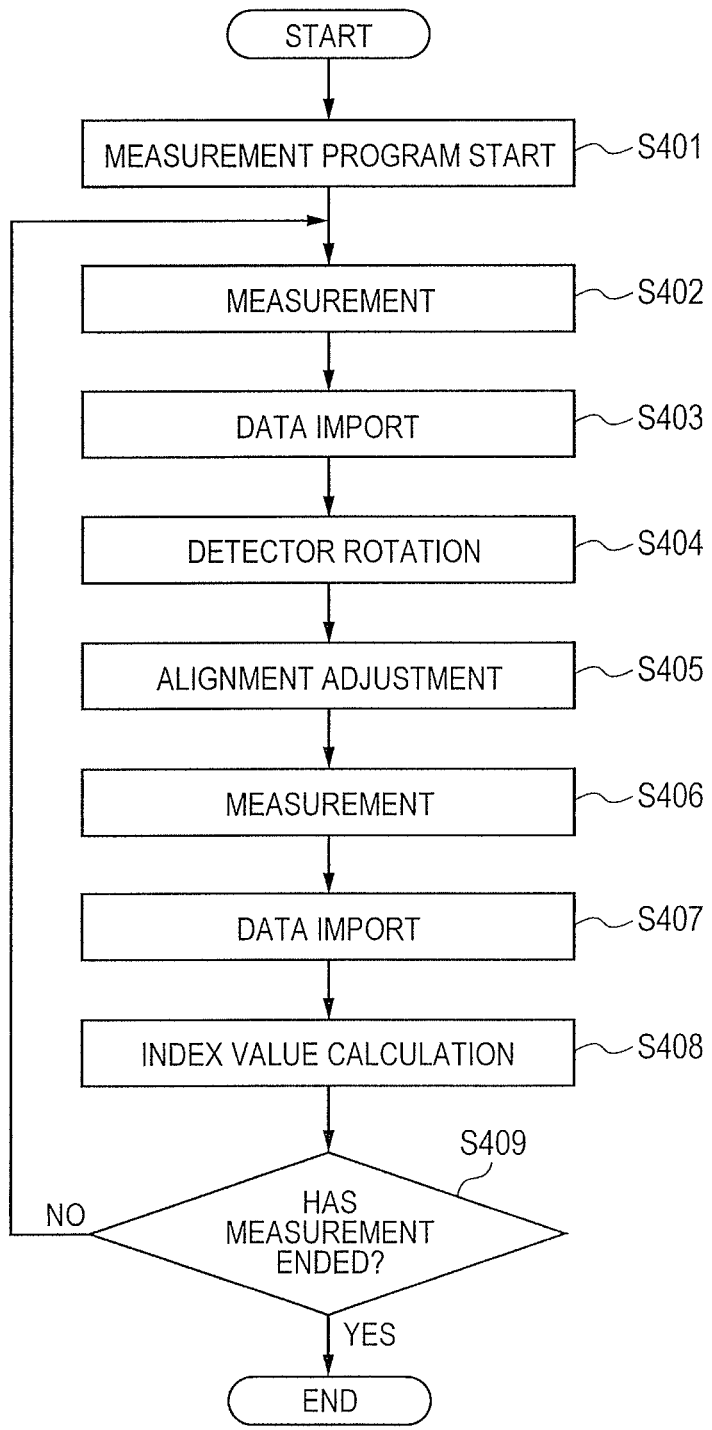
FIG. 30 is a flow chart showing an inspection method according to the fourth embodiment of the present invention.

Subsequently, with reference to the flow chart in FIG. 30, an inspection method using the inspection apparatus according to the embodiment will be explained.

First, the sample 3 that is an inspection object is set to the optical device 2a. On this occasion, the angle of the sample 3 relative to the optical device 2a is adjusted so that terahertz-waves from the sample 3 passes through the diaphragm 19. When an operator operates the control unit 5 to start the inspection program, the CPU 503 executes the inspection program stored in the external memory 506 and initializes the optical device 2a, the lock-in amplifier 4, and the control unit 5 (Step S401). The control unit 5a drives the actuator 24 to adjust the angle of the terahertz-wave detector 22 so that the terahertz-wave detector 22 detects the horizontally polarized light.

Subsequently, the inspection apparatus 1a performs the measurement according to a procedure below (Step S402). First, the light pulse of the femtosecond fiber laser 10 is divided into the fundamental wave of 1550 nm component and the second harmonic wave of the 780 nm component by the dichroic mirror 11, and the fundamental wave enters the chopper 12 and the second harmonic wave enters the optical delay part 25. The chopper 12 modulates the fundamental wave at a prescribed modulation frequency. The modulated fundamental wave is reflected by the mirror 13 and the paraboloidal mirror 14 for condensing the fundamental wave, and, after that, is condensed to the DAST 15. The terahertz-wave generated by the DAST 15 is reflected by off-axis paraboloidal mirrors 16 and 17, and is condensed to the metallic coated sample 3.

The polarized light of the terahertz-wave reflected by the metallic coated sample 3 is disturbed by flakes inside the metallic coating. The terahertz-wave in which the polarized light has been disturbed passes through the opening part of the diaphragm 19A, collimated by the off-axis paraboloidal mirror 18, and furthermore passes through the opening part of the diaphragm 19B. On this occasion, reflected waves of the periphery part of the terahertz-wave are intercepted.

Terahertz-waves having passed through the diaphragm 19B is condensed to the terahertz-wave detector 22 by the off-axis paraboloidal mirror 20. Incidentally, the pulse of terahertz-waves is condensed repeatedly to the terahertz-wave detector 22 at the modulation frequency (1 kHz). On the other hand, the probe light delayed by a prescribed time by the optical delay part 25 is irradiated to the gap of the dipole antenna by the condenser lens 23. At this time, a micro electric current proportional to the electric field of the terahertz-wave flows, and the micro current is synchronously detected by the lock-in amplifier 4. The lock-in amplifier 4 converts the amplified current to digital data by an A/D converter to record the same on a memory. Consequently, the intensity of the wave form of the terahertz-wave at a prescribed timing is measured.

When sampling the wave form of the terahertz-wave, the electric field intensity in the terahertz-wave detector 22 is measured while moving the timing of the probe light. That is, as shown in FIG. 14, the control unit 5a drives the movable mirror of the optical delay part 25, and set the delay time of the probe light to be t1. The probe light is condensed to the terahertz-wave detector 22, and the electric field intensity of the terahertz-wave at the timing of delay time t1 is measured. Subsequently, the control unit 5a sets the delay time in the optical delay part 25 to be t2, and the terahertz-wave detector 22 detects the electric field intensity of the terahertz-wave at the timing. In the same manner, by changing delay times in the optical delay part 25 in order of t3, t4, t5 ..., the sampling of the wave form of the terahertz-wave becomes possible. The control unit 5a imports the measured data representing the wave form of the terahertz-wave, and stores the same on the memory 506 (Step S403).

Subsequently, the control unit 5a drives the actuator 24 to rotate the terahertz-wave detector 22 in 45° relative to the horizontal direction (Step S404). On this occasion, the control unit 5 adjusts the alignment of the terahertz-wave detector 22 so that the terahertz-wave condensed to the terahertz-wave detector 22 falls at the gap part of the dipole antenna (Step S405).

After the completion of the rotation of the terahertz-wave detector 22 and the adjustment of the alignment, the optical device 2a repeats above-mentioned movements. That is, the optical device 2a samples the terahertz-wave in the terahertz-wave detection part 22, while changing the delay time of probe light in the optical delay part 25 (Step S406). The control unit 5a imports data representing the wave form of the terahertz-wave in the memory 508 (Step S407).

After the measurement of wave form data of terahertz-waves at each of polarization angles of 0° and 45°, the control unit 5 shows visually measured data on the display 506.

Figure 35:
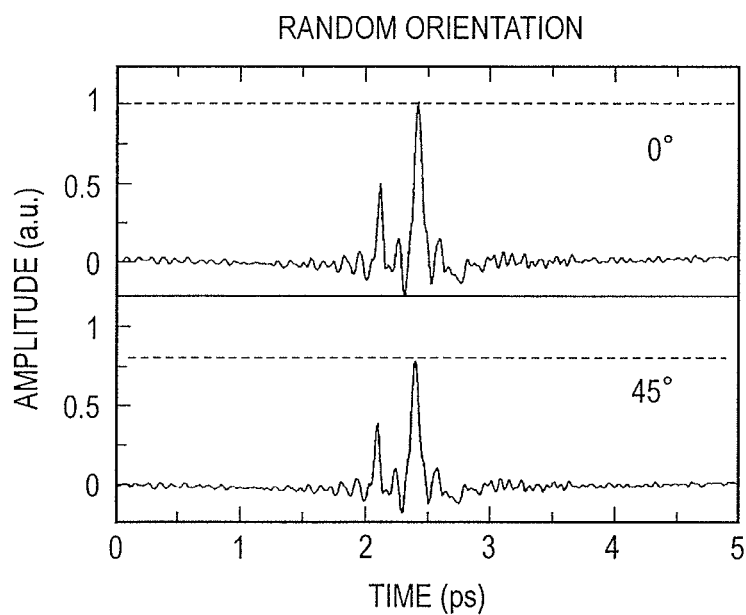
FIG. 35 is a graph showing an example of the inspection result according to the present invention.
Figure 36:
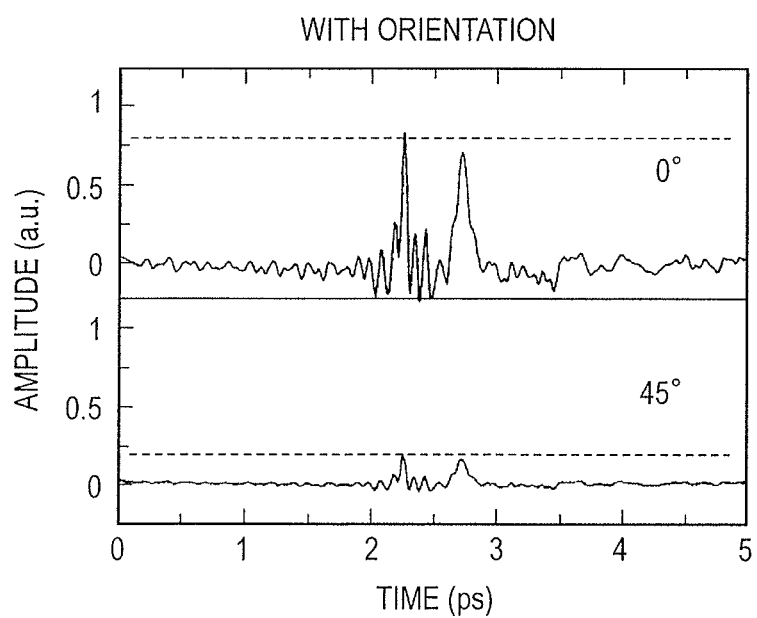
FIG. 36 is a graph showing an example of the inspection result according to the present invention.

FIGS. 35 and 36 show specific examples of measured data. FIG. 35 shows the wave form of the terahertz-wave when flakes in the metallic coated sample 3 are oriented randomly, and FIG. 36 shows the wave form of the terahertz-wave when flakes are oriented in a specified direction. In these drawings, the upper stage shows the wave form of the terahertz-wave when the polarization angle is 0°, and the lower stage shows the wave form of the terahertz-wave when the polarization angle is 45°. The vertical axis represents the intensity of terahertz-waves, the horizontal axis represents the delay time. Flakes in the metallic coated sample 3 are arranged randomly in an ideal state, and polarization of reflected terahertz-waves is also disturbed. Therefore, the intensity of respective components of polarization angles 0° and 45° in reflected terahertz-waves is approximated one. Incidentally, the component at the polarization angle 0° is slightly stronger than the component at 45°, which is caused by the fact that terahertz-waves generated by the DAST 15 is linearly-polarized light.

On the other hand, when defect on external appearance such as hue unevenness exists in the sample 3, flakes are oriented in a specified direction. In such a case, the metallic coated sample 3 is equivalent to a reflective element having polarization properties such as a diffraction grating in the frequency region of terahertz-waves. Accordingly, as shown in FIG. 36, a polarization component of a specified angle is strong in reflected terahertz-waves.

An operator can decide whether the sample 3 is good or bad, while confirming measured data shown on the display 506. Further, it is also possible to express numerically the degree of randomness of flake orientation of the metallic coated sample 3 as an index value, and to decide automatically the good or bad of the sample 3 by the control unit 5 (Step S408). The index value can be calculated by a method below. For example, it is possible to use the difference or the ratio of intensities of two polarization components (for example, peak values of the wave form) at a prescribed timing of the terahertz-wave as the index value. Or, it is also possible to grasp the wave form of terahertz-waves as a function of time and use the correlation of two functions (wave forms) as an index value.

The control unit 5a can decide automatically good or bad of the sample 3, by comparing the index value calculated from the measured data with a previously determined value. When the index value calculated from the measured data is larger than a previously determined value, that is, when the degree of randomness of flake orientation is high, the control unit 5a decides that the sample 3 is a good product. On the other hand, when the measured data are not more than a previously determined index value, that is, when the degree of randomness of the flake orientation is low, the control unit 5a decides that the sample 3 is a defective product.

Furthermore, in the same manner as in the first embodiment, the control unit 5a may perform film thickness measurement. That is, it detects peaks from wave form data on the basis of a previously input peak pattern, film thickness range and intensity ratio range, and calculates the film thickness from the delay time between peaks.

The inspection result thus obtained is displayed on the display 508 with measured data. After performing the above processing, when measurement is to be performed continuously (YES in Step S409), the control unit 5a performs repeatedly the processing of Steps S401 to S408. On the other hand, when the measurement has been terminated (NO in Step S409), the control unit 5a terminates the processing.

As described above, according to the embodiment, it is possible to eliminate components of terahertz-waves having time delay, by intercepting the periphery light of terahertz-light reflected at a sample by the diaphragm. Consequently, it becomes possible to improve lowering of detection resolution caused by a curved surface, island-shaped materials etc.

In addition, it becomes possible to inspect the state of flake orientation without performing statistical processing, by making terahertz-waves be reflected by a metallic coating and measuring a polarization component of half-reflected terahertz-waves. Consequently, a metallic coating can be inspected precisely in short time. And, since terahertz-waves have such nature as passing through resin, even resin through which visible light does not pass may be inspected. Furthermore, since noncontact inspection becomes possible for metallic coatings, precise inspection can be performed not only in a dry state but also in a wet state directly after coating.

Fifth Embodiment

Figure 31:
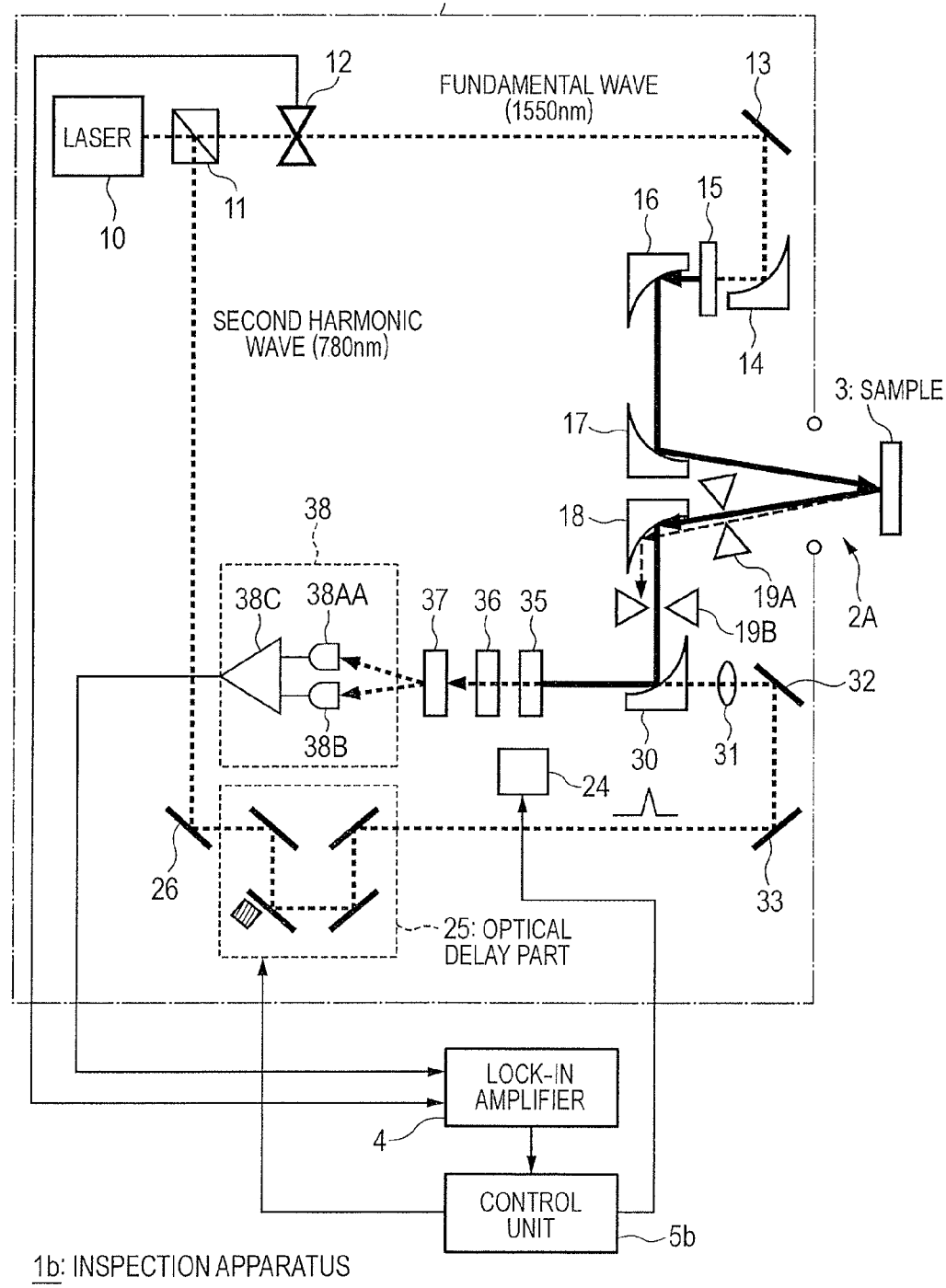
FIG. 31 is a block diagram of an inspection apparatus according to a fifth embodiment of the present invention.

FIG. 31 is the block diagram of the inspection apparatus 1b of metallic coatings according to the fifth embodiment of the present invention. The inspection apparatus 1b is configured by including an optical device 2b, the lock-in amplifier 4, and the control unit 5. The inspection apparatus according to the embodiment uses an EO (electro-optic) crystal 35 as a terahertz-wave detector, differing from the fourth embodiment, and detects two polarization components of terahertz-waves by rotating the EO crystal 35 in 45°.

(Configuration of Optical Device)

The optical device 2b includes the femtosecond fiber laser 10, the dichroic mirror 11, the chopper 12, mirrors 13, 26, 32 and 33, the paraboloidal mirror 14 for condensing fundamental waves, the DAST 15, off-axis paraboloidal mirrors 16, 17, 18 and 30, the diaphragm 19, the actuator 24, the optical delay part 25, the EO crystal 35, a λ/4 plate 36, a wollaston prism 37 and a balanced detector 38. In the embodiment, since members to which the same reference numeral as the reference numeral in the first embodiment is given are configured in the same manner as in the fourth embodiment, explanation will given with a central focus on members different from those in the fourth embodiment.

For the off-axis paraboloidal mirror 30, a through-hole is provided, and probe light having been condensed by the lens 31 enters the through-hole. The probe light having passed the through-hole is irradiated to the EO crystal 35.

The EO crystal 35 includes a semiconductor such as ZnTe, and has a crystal axis in a prescribed direction (<100> direction in the case of ZnTe). To the EO crystal 35, the terahertz-wave condensed by the off-axis paraboloidal mirror 30, and the probe light delayed by the optical delay part 25 are irradiated. Only when the terahertz-wave overlaps temporally with the probe light in the EO crystal 35, the probe light is subjected to an electro-optic effect by the terahertz-wave (birefringence), and the probe light of linearly-polarized light is turned into elliptically-polarized light. Since the amount of birefringence is proportional to the electric field intensity of terahertz-pulse waves, by detecting the probe light having passed through the EO crystal 35, the intensity of the terahertz-pulse wave can be measured.

The λ/4 wavelength plate 36 includes an anisotropic crystal, and changes the probe light into circularly-polarized light by making the velocity travelling the inside thereof change according to the polarization direction.

The wollaston prism 37 is a polarizing prism, for example, consisting of calcite, and has such a function as to separate incident probe light into two polarization components. Here, separated two polarization components depend on the direction and intensity of the electric field of the terahertz-wave.

Balanced detector 38 is configured, including photodiodes 38A and 38B, and a differential amplifier 38C. To photodiodes 38A and 38B, polarization components separate by the wollaston prism 37 are entered, and output that is proportional to the intensity of the polarization component is output from photodiodes 38A and 38B. The differential amplifier 38C amplifies the difference between each output. In the case of complete circularly-polarized light, the difference is zero. But, in such a case as elliptically-polarized light, a difference occurs and is amplified by the differential amplifier 38C. The signal after the amplification is output to the lock-in amplifier 4.

Since other configuration in the optical device 2b is the same as that in the optical device 2a in the fourth embodiment, the explanation thereof is omitted. Incidentally, also in the embodiment, it is desirable that the optical device 2b is sealed from the outside by a housing, and that the inside of the housing is dehumidified, filled with nitrogen gas, or evacuated.

(Inspection Method)

Figure 32:
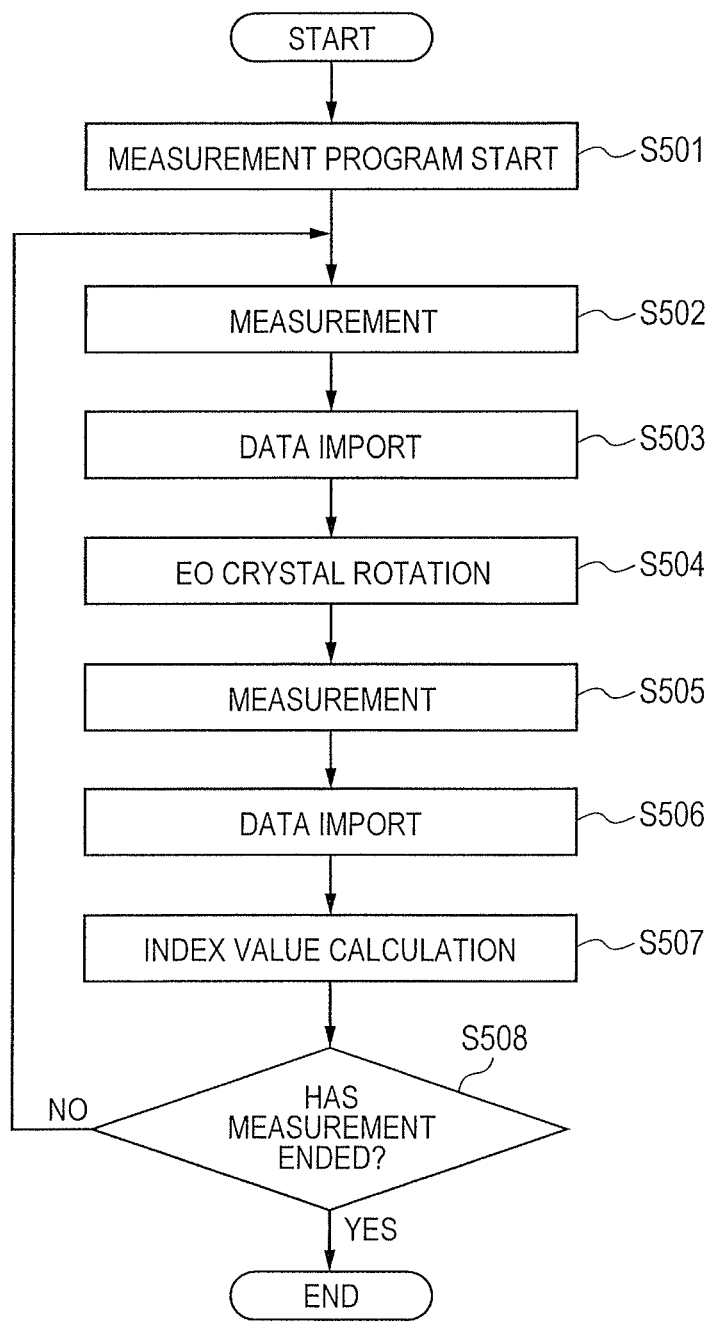
FIG. 32 is a flow chart showing an inspection method according to the fifth embodiment of the present invention.

Subsequently, with reference to the flow chart in FIG. 32, an inspection method using the inspection apparatus according to the embodiment will be explained.

First, after setting the sample 3 to be an inspection object to the optical device 2b, the angle of the EO crystal 35 is adjusted so that the crystal axis of the EO crystal 35 coincides with the polarization direction of terahertz-waves. The adjustment of rotation angle of the EO crystal 35 may be performed by the actuator 24 that is driven by the control unit 5b. An operator operates the control unit 5b to start the inspection program (Step S501), and the inspection apparatus 1b performs measurement according to a procedure below (Step S502).

The light pulse of the femtosecond fiber laser 10 is separated into the fundamental wave of the 1550 nm component and the second harmonic wave of the 780 nm component in the dichroic mirror 11, wherein the fundamental wave is made to enter the chopper 12 and the second harmonic wave is made to enter the optical delay part 25. The chopper 12 modulates the fundamental wave at a prescribed modulation frequency, and the modulated fundamental wave is reflected by the mirror 13 and the paraboloidal mirror 14 for condensing the fundamental wave, and, after that, is condensed to the DAST 15. Terahertz-waves generated by the DAST 15 is reflected by off-axis paraboloidal mirrors 16 and 17 to be condensed in the sample 3.

The polarization of terahertz-waves reflected by the sample 3 is disturbed by flakes inside the metallic coating. The terahertz-wave in which the polarization has been disturbed passes through the diaphragm 19A, and then is collimated by the off-axis paraboloidal mirror 18 to pass through the opening part of the diaphragm 19B. Reflected waves of periphery part of the terahertz-wave are intercepted by diaphragms 19A and 19B.

The terahertz-wave having passed through the diaphragm 19B is condensed to the EO crystal 35 by the off-axis paraboloidal mirror 30. On the other hand, the light pulse that is a probe light having been delayed by a prescribed time by the optical delay part 25 is reflected by mirrors 33 and 32, is condensed by the lens 31, and then passes through the through-hole of the off-axis paraboloidal mirror 30. The probe light having passed through the through-hole is irradiated to the EO crystal 35.

Only when the terahertz-wave overlaps temporally with the probe light in the EO crystal 35, the probe light is subjected to an electro-optic effect by the terahertz-wave (birefringence), and the probe light of linearly-polarized light is turned into elliptically-polarized light.

The λ/4 wavelength plate 36 changes the probe light into circularly-polarized light, and the wollaston prism 37 separates incident probe light into two polarization components. As described above, separated two polarization components depend on the direction and intensity of the electric field of the terahertz-wave. The balanced detector 38 amplifies the difference of polarization components separated by the wollaston prism 37 and outputs the same to the lock-in amplifier 4 as a detection signal. The lock-in amplifier 4 performs the amplification of the detection signal by performing synchronous detection according to the modulation frequency. The lock-in amplifier 4 converts the amplified current into digital data by an A/D convertor and records the same on a memory. Consequently, the intensity of wave form of terahertz-waves at a prescribed timing is measured.

Furthermore, when sampling the wave form of terahertz-waves, the electric field intensity in the EO crystal 35 is measured, while moving the timing of the probe light by the optical delay part 25. The control unit 5 imports measured data showing the wave form of terahertz-waves and stores the same on the memory 506 (Step S503).

Subsequently, the control unit 5b drives the actuator 24, and rotates the EO crystal 35 in 45' relative to the horizontal direction (Step S504). In the embodiment, there is no necessity of performing the alignment adjustment of the EO crystal 35 after rotating the EO crystal 35. Because, on the condition that the EO crystal 35 has a uniform crystal, uniform non-linear susceptibility is obtained in any position of the EO crystal 35. Accordingly, there is no necessity of adjusting the gap of the dipole antenna, differing from the fourth embodiment, and effective inspection becomes possible.

After rotating the EO crystal 35, the optical device 2b repeats the above-mentioned operation to measure terahertz-waves (Step S505). The control unit 5b imports data that represents the wave form of terahertz-waves into the memory 508 (Step S506).

Furthermore, in the same manner as in the first embodiment, the control unit 5b performs film thickness measurement. That is, on the basis of previously input peak pattern, film thickness range and intensity range, it detects peaks from wave form data to calculate film thickness from the delay time between peaks.

After performing the measurement of wave form data of terahertz-waves at each of polarization angles 0° and 45°, the control unit 5b displays visually the measured data on the display 506. Furthermore, the control unit 5 calculates the difference or ratio of respective measurement results at two angles 0° and 45° of the EO crystal 35 as an index value (Step S507).

In the embodiment, since the signal that is proportional the intensity of terahertz-waves is detected depending on the relation between the crystal axis of the EO crystal 35 and the polarization direction of terahertz-waves, it is possible to decide good or bad of the metallic coating 3 on the basis of the index value. FIGS. 33A, 33B, 34A and 34B show the relation between the crystal axis of the EO crystal 35 and the polarization direction of terahertz-waves. When denoting the travelling direction of terahertz-waves by the direction perpendicular to the paper, the polarization direction of terahertz-waves is shown by a solid arrow. A dotted arrow shows the crystal axis direction.

Figure 33A:
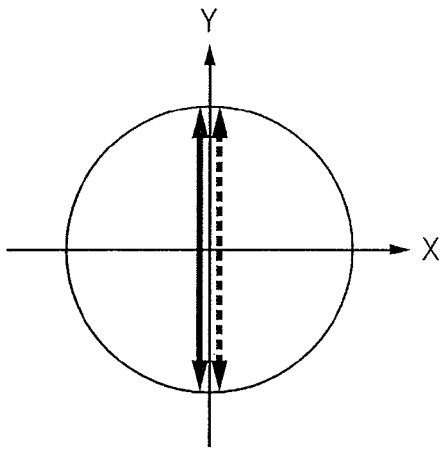
FIG. 33A is a drawing for explaining a polarization direction and a crystal axis direction in an electro-optic (EO) crystal according to the fifth embodiment of the present invention.
Figure 33B:
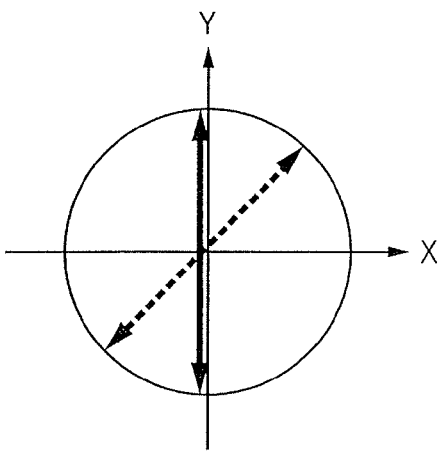
FIG. 33B is a drawing for explaining the polarization direction and the crystal axis direction in an electro-optic (EO) crystal according to the fifth embodiment of the present invention.

As shown in FIG. 33A, when terahertz-waves have linear polarization, under the optimal condition, the polarization direction of terahertz-waves coincides with the crystal axis of the EO crystal 35 (<100> direction in ZnTe). And, as shown in FIG. 33B, when the crystal axis is inclined in 45° relative to the polarization direction of terahertz-waves, the sensitivity of the EO crystal 35 becomes a projection component on the Y axis, which is ½ theoretically.

Figure 34A:
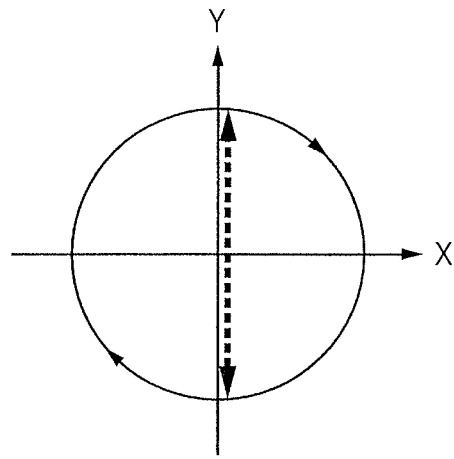
FIG. 34A is a drawing for explaining the polarization direction and the crystal axis direction in an electro-optic (EO) crystal according to the fifth embodiment of the present invention.
Figure 34B:
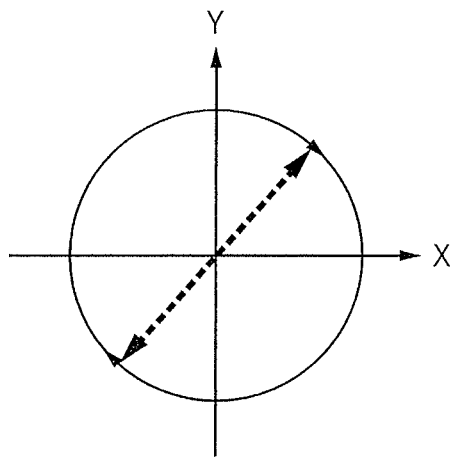
FIG. 34B is a drawing for explaining the polarization direction and the crystal axis direction in an electro-optic (EO) crystal according to the fifth embodiment of the present invention.

On the other hand, as shown in FIG. 34A, when terahertz-waves have circularly-polarized light, the polarization direction of terahertz-waves does not completely coincides with the crystal axis, and the sensitivity of the EO crystal 35 becomes the projection component on the Y axis. And, as shown in FIG. 34B, even when the crystal axis is inclined in 45° relative to the varying component of terahertz-waves, the sensitivity of the EO crystal 35 does not change. Accordingly, measured values in respective cases of two angles 0° and 45° of the EO crystal 35 also coincide each other.

Flakes of the metallic coated sample 3 are arranged randomly in an ideal state, and the polarization of reflected terahertz-waves is disturbed, too. Therefore, reflected terahertz-waves approaches circularly-polarized light. But, actually, since the terahertz-wave generated by the DAST 15 is of linear polarization, the reflected terahertz-wave is not complete circularly-polarized light, but is elliptically-polarized light. By comparing the index value when flakes of the metallic coated sample 3 are arranged in the best state with the index value on the basis of actual measured data, good or bad of the metallic coated sample 3 may be decided automatically.

It is also possible to use the difference or ratio between intensities of two polarization components (for example, peak values of wave form) of terahertz-waves at a prescribed timing as an index value, or to grasp the wave form of terahertz-waves as a function of time and to use the correlation of two functions (wave forms) as an index value.

In the embodiment, too, in the same manner as in the third embodiment, it is possible to inspect good or bad of the flake orientation, at the same time as film thickness measurement. And, by making terahertz-waves be reflected by a metallic coating and measuring the polarization component of half-reflected terahertz-waves, it becomes possible to inspect the flake orientation state without performing statistic processing. Consequently, the inspection of a metallic coating can be performed precisely in a short time. And, since terahertz-waves have such nature as passing through resin, even resin through which visible light does not pass may be inspected. Furthermore, since noncontact inspection becomes possible for metallic coatings, precise inspection can be performed not only in a dry state but also in a wet state directly after coating.

In the embodiment, the terahertz-wave detector 22, and the EO crystal 35 are rotated in 45°. But, they may be rotated in an arbitrary angle, only if the disturbance of polarization of terahertz-waves can be detected. The polarization component to be measured is not limited to two kinds, but polarization component not less than three kinds may be measured. Furthermore, it is also acceptable that the terahertz-wave detector 22 and the EO crystal 35 are not rotated, but that polarization of terahertz-waves are rotated using a half-wavelength plate relative to the terahertz-wave. The kind of detector is also not limited, only if it can detect the polarization component of terahertz-waves reflected by a metallic coated sample.

According to the coating film inspection apparatus according to the embodiment, it is possible to eliminate components of terahertz-waves having time delay, by intercepting the periphery light of terahertz-light reflected at a sample by the diaphragm. Consequently, it becomes possible to improve lowering of detection resolution caused by a curved surface, island-shaped materials etc.

Since the coating film inspection apparatus according to the embodiment uses an EO crystal as detection means, there is no necessity to perform alignment adjustment after rotating the EO crystal, to make effective measurement possible.

The present invention is not limited to above-mentioned embodiments, and may be changed in a range that does not deviate from the purport of the present invention. For example, the present invention is not limited to the thickness measurement of metallic coating films, but is applicable to the measurement of any kind of films, such as coated films formed on a foundation, protective films, electroconductive films and insulating films.

This application claims the priorities based on Japanese Patent Application No. 2010-042492 filed on Feb. 26, 2010 and Japanese Patent Application No. 2010-281408 filed on Dec. 17, 2010, and the contents thereof are incorporated herein by reference.

The invention claimed is:
1. A coating film inspection apparatus, comprising:
   a terahertz-wave generator that generates a terahertz-wave;
   an irradiation optical system that irradiates a metallic coated sample with the terahertz-wave;
   a terahertz-wave detector that detects a plurality of polarization components of a terahertz-wave reflected at the sample; and
   a control unit that calculates an index value of the metallic coated sample on the basis of the detected plurality of polarization components; and
   rotation means that makes it possible to detect the plurality of polarization components by rotating the terahertz-wave detector by a prescribed angle relative to a light axis of the reflected terahertz-wave.

2. The coating film inspection apparatus according to claim 1, wherein the prescribed angle is approximately 45°, and the terahertz-wave detector detects two polarization components before and after the rotation.

3. The coating film inspection apparatus according to claim 1, wherein the terahertz-wave detector includes a dipole antenna-type detector.

4. The coating film inspection apparatus according to claim 1, wherein the terahertz-wave detector includes an EO crystal.

* * * * *